United States Patent
Tsukada et al.

(10) Patent No.: US 10,416,184 B2
(45) Date of Patent: Sep. 17, 2019

(54) PRETREATMENT DEVICE FOR SAMPLE FOR ANALYSIS, AND ANALYSIS SYSTEM USING SAME

(71) Applicant: Hitachi, Ltd., Chiyoda-ku, Tokyo (JP)

(72) Inventors: Nobuhiro Tsukada, Tokyo (JP); Ayano Otsubo, Tokyo (JP); Yoshihiro Nagaoka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 168 days.

(21) Appl. No.: 15/037,206

(22) PCT Filed: Nov. 28, 2013

(86) PCT No.: PCT/JP2013/082051
§ 371 (c)(1),
(2) Date: May 17, 2016

(87) PCT Pub. No.: WO2015/079534
PCT Pub. Date: Jun. 4, 2015

(65) Prior Publication Data
US 2016/0299168 A1    Oct. 13, 2016

(51) Int. Cl.
  *G01N 35/10*   (2006.01)
  *B01L 3/00*    (2006.01)
  *G01N 35/00*   (2006.01)

(52) U.S. Cl.
  CPC .... *G01N 35/1097* (2013.01); *B01L 3/502715* (2013.01); *G01N 35/1004* (2013.01);
  (Continued)

(58) Field of Classification Search
  CPC ................................................. G01N 35/1097
  See application file for complete search history.

(56) References Cited

U.S. PATENT DOCUMENTS

| | | | |
|---|---|---|---|
| 3,615,234 A | 10/1971 | Ludvigsen | |
| 3,880,011 A * | 4/1975 | Johnson | G01N 1/14 222/205 |

(Continued)

FOREIGN PATENT DOCUMENTS

| | | |
|---|---|---|
| JP | 53-106090 | 9/1978 |
| JP | 54-2869 B1 | 2/1979 |
| JP | 9-218204 A | 8/1997 |

OTHER PUBLICATIONS

Japanese-language Office Action issued in counterpart Japanese Application No. 2015-550268 dated Mar. 21, 2017 with English translation (Ten (10) pages).

(Continued)

*Primary Examiner* — Matthew D Krcha
(74) *Attorney, Agent, or Firm* — Crowell & Moring LLP

(57) ABSTRACT

The present invention provides a pretreatment device for a sample for analysis that makes it possible to send a sample liquid to an arbitrary treatment module connected to a sample liquid conveyance flow route, and an analysis system using the same. A pretreatment device for a sample for analysis according to the present invention is at least provided with a plurality of sample liquid treatment modules for introducing a sample liquid or carrying out prescribed pretreatment on the sample liquid, a first flow path for conveying the sample liquid or the pretreated sample liquid between the plurality of sample liquid treatment modules, and a conveyance direction switching part for switching the conveyance direction of the sample liquid or the pretreated sample liquid in the first flow path. The sample liquid treatment modules have an introduction flow path for introducing the sample liquid or the pretreated sample liquid from the first flow path, a discharge flow path for sending the sample liquid or the pretreated sample liquid to the first flow path, and a flow path switching part for switching the state (Continued)

of communication with the first flow path of the introduction flow path and the discharge flow path.

12 Claims, 18 Drawing Sheets

(52) U.S. Cl.
CPC ... *B01L 2200/027* (2013.01); *B01L 2200/143* (2013.01); *B01L 2300/0627* (2013.01); *B01L 2300/0645* (2013.01); *B01L 2300/0822* (2013.01); *B01L 2300/0867* (2013.01); *B01L 2400/0622* (2013.01); *G01N 2035/00326* (2013.01)

(56) References Cited

U.S. PATENT DOCUMENTS

| | | | |
|---|---|---|---|
| 4,224,033 A | 9/1980 | Hansen et al. | |
| 4,520,108 A * | 5/1985 | Yoshida | G01N 35/085 422/503 |
| 4,722,830 A * | 2/1988 | Urie | G01N 35/08 422/503 |
| 5,783,740 A | 7/1998 | Tawarayama et al. | |
| 6,387,328 B1 | 5/2002 | Berndtsson | |
| 2006/0073605 A1* | 4/2006 | Horan | G01N 31/005 436/155 |
| 2007/0125170 A1* | 6/2007 | Tenney | G01F 23/14 73/290 R |
| 2008/0154543 A1* | 6/2008 | Rajagopal | G01N 35/00 702/183 |
| 2012/0122705 A1* | 5/2012 | Ting | G01N 1/286 506/7 |

OTHER PUBLICATIONS

International Search Report (PCT/ISA/210) issued in PCT Application No. PCT/JP2013/082051 dated Feb. 10, 2014 with English-language translation (three (3) pages).

* cited by examiner

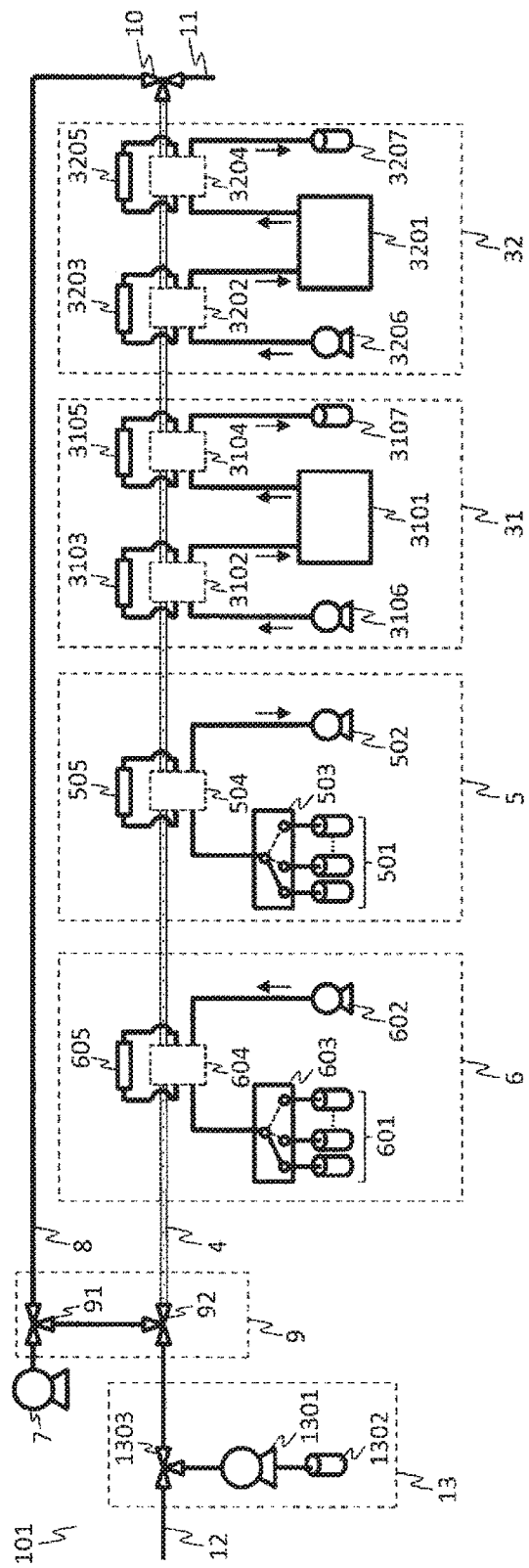
[Fig. 1]

[Fig. 2]
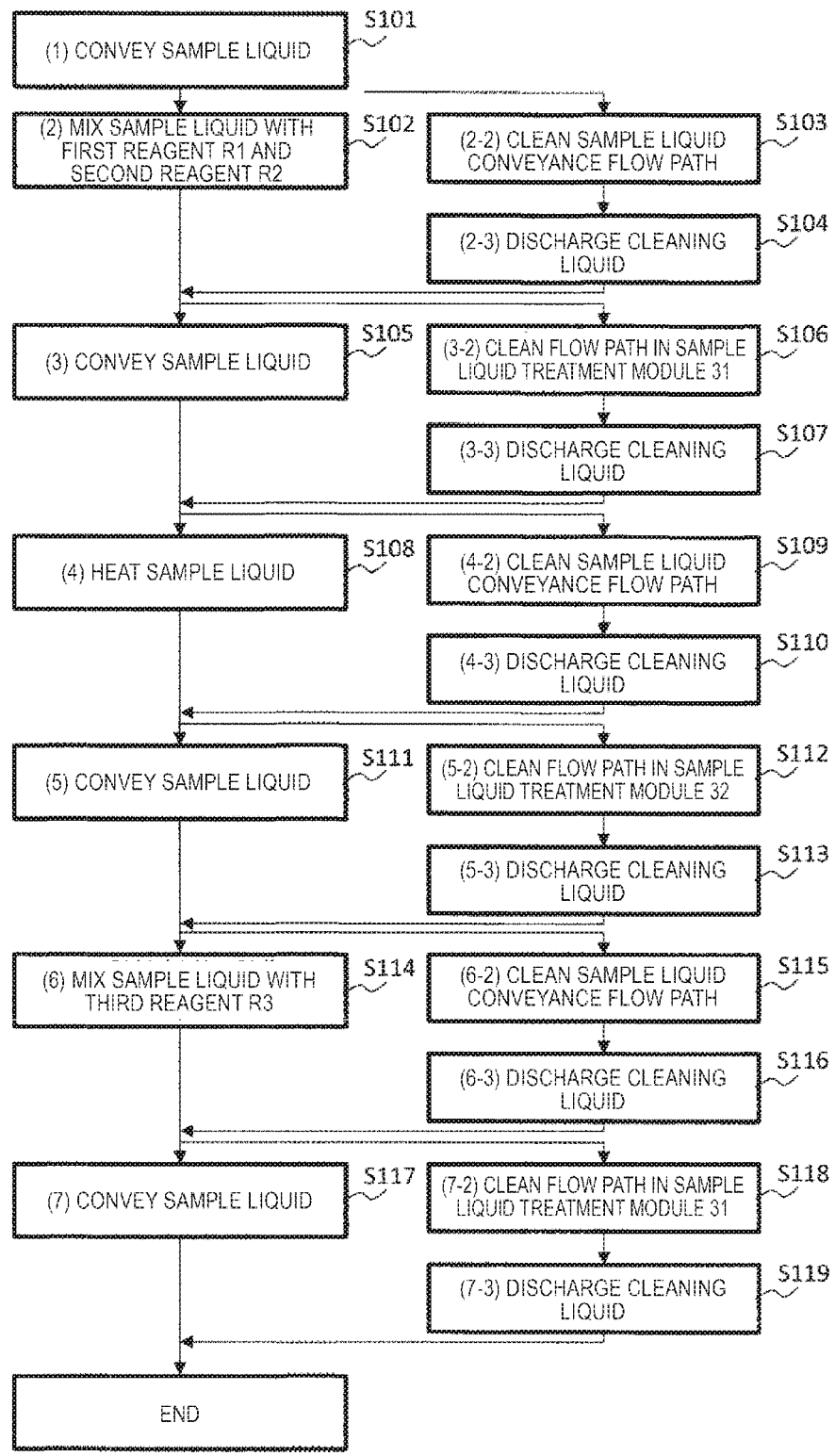

FIG. 5C
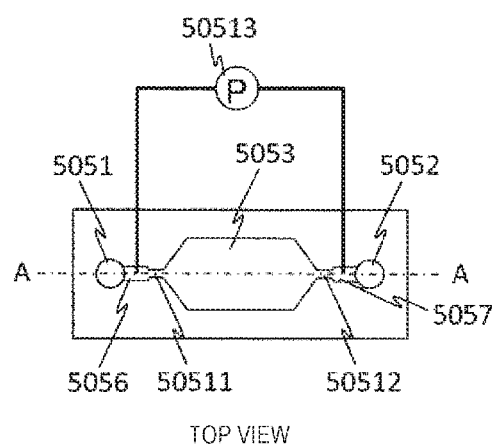
TOP VIEW
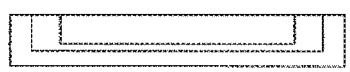
A-A SECTIONAL VIEW

[Fig. 7]
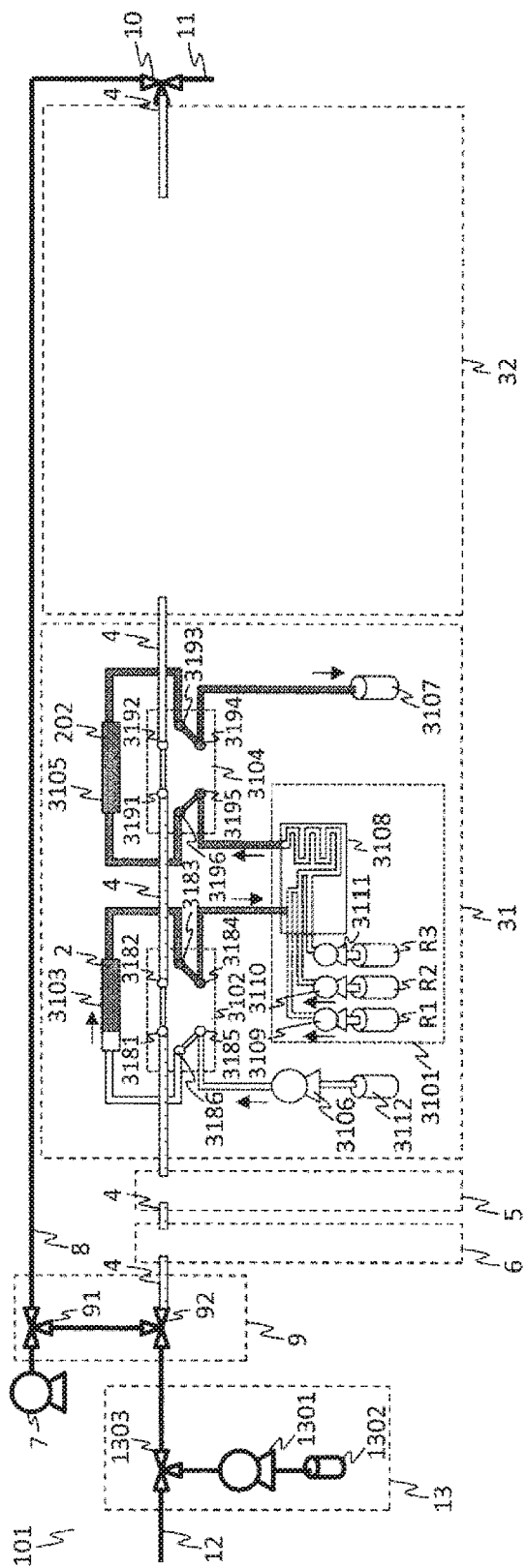

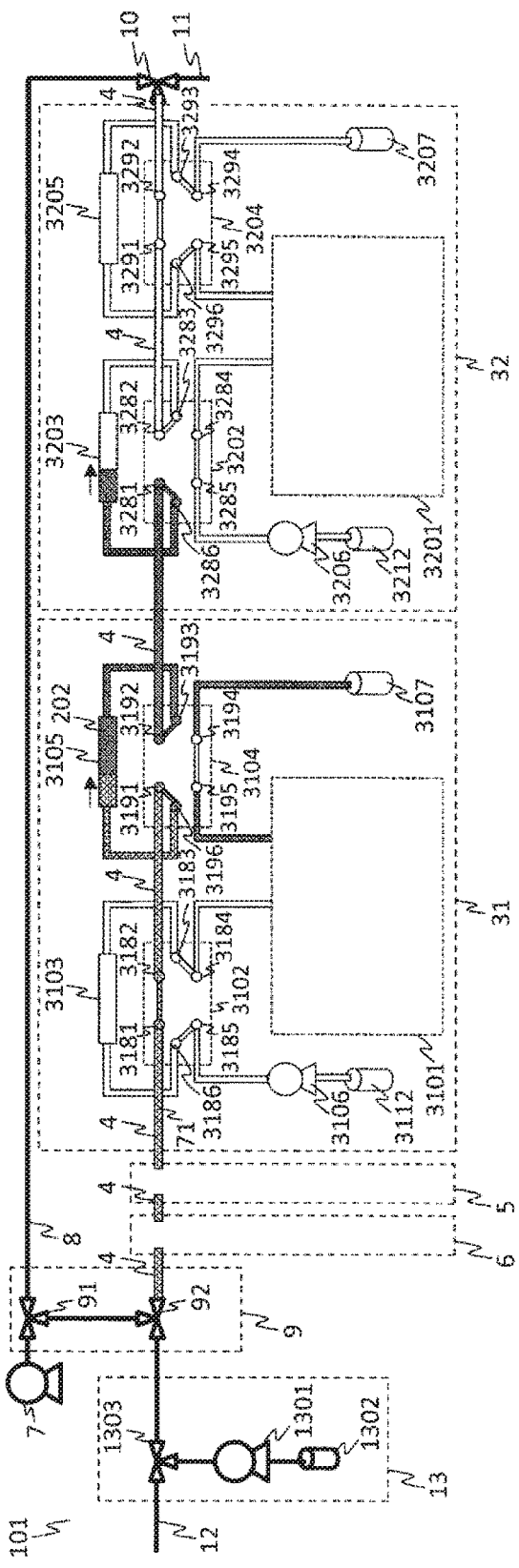
[Fig. 8]

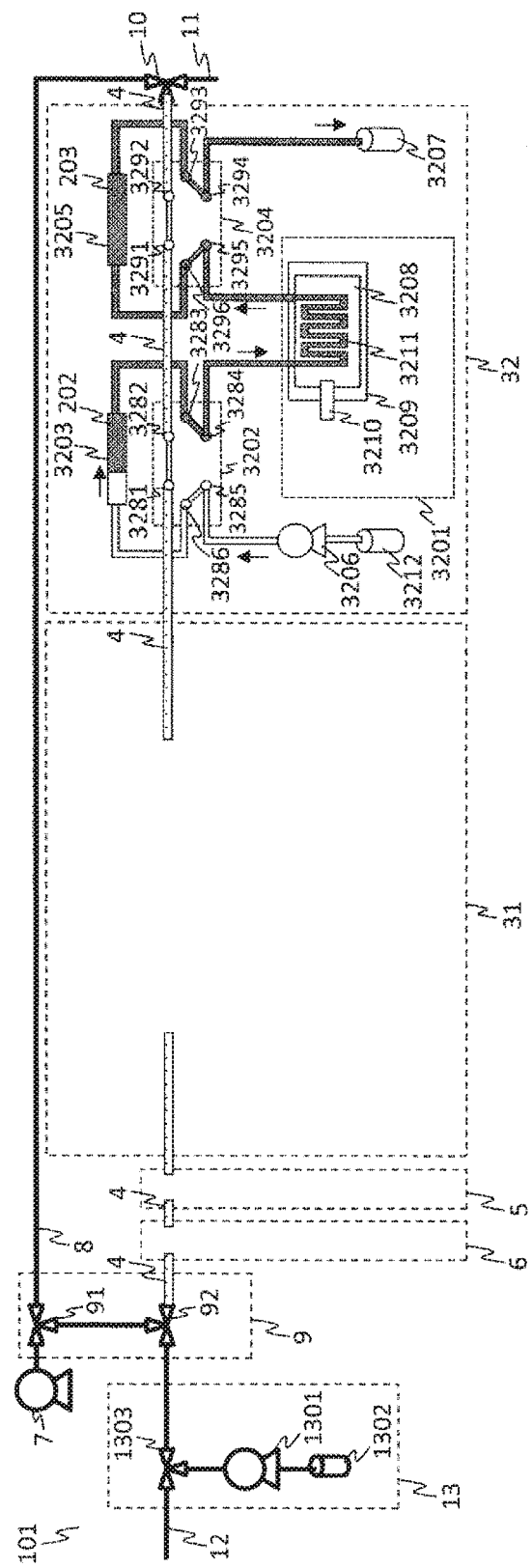
[Fig. 9]

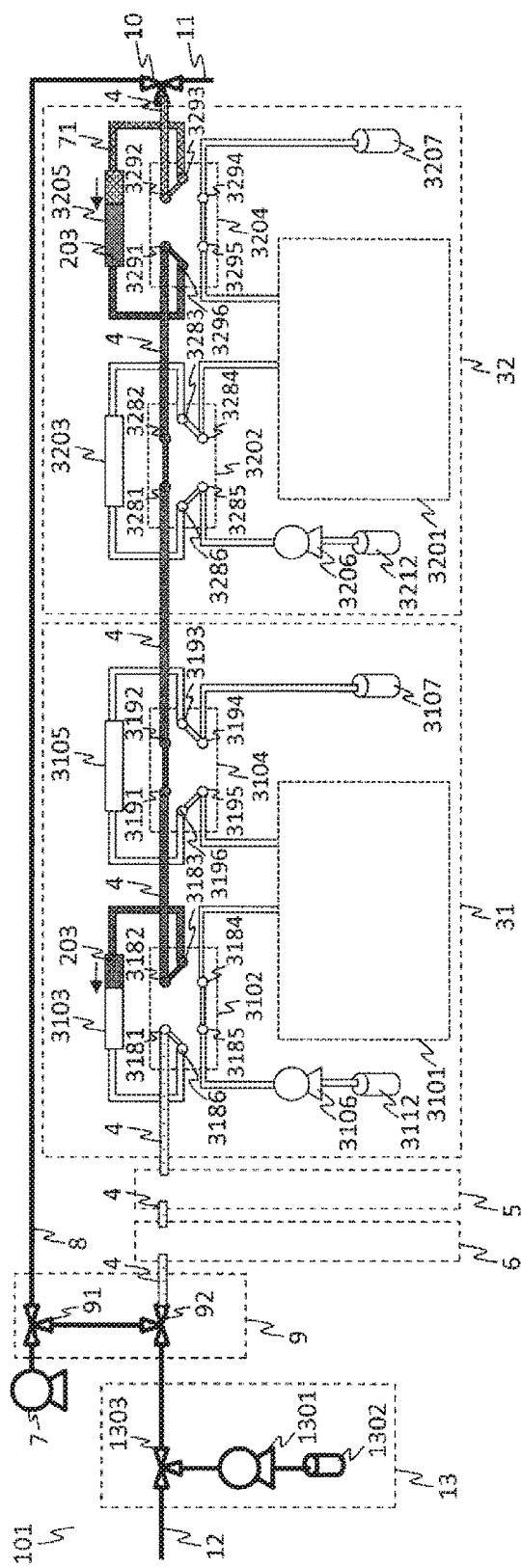
[Fig. 10]

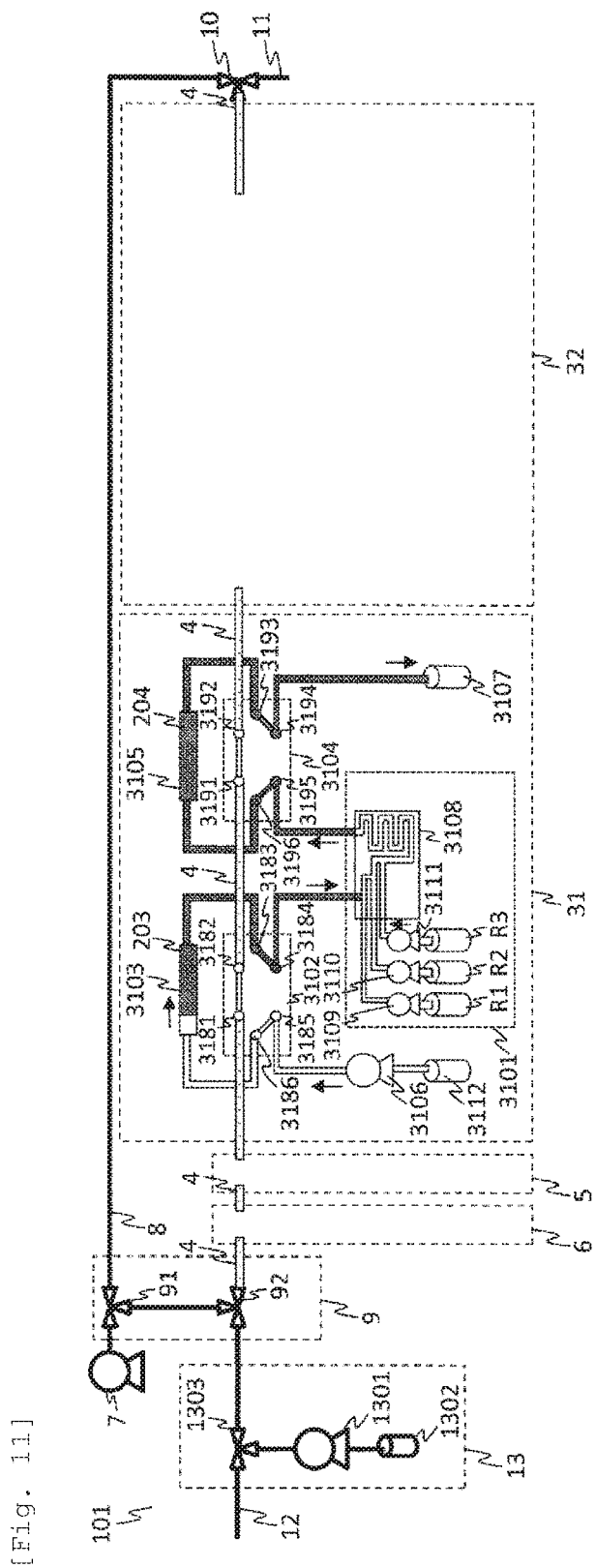
[Fig. 11]

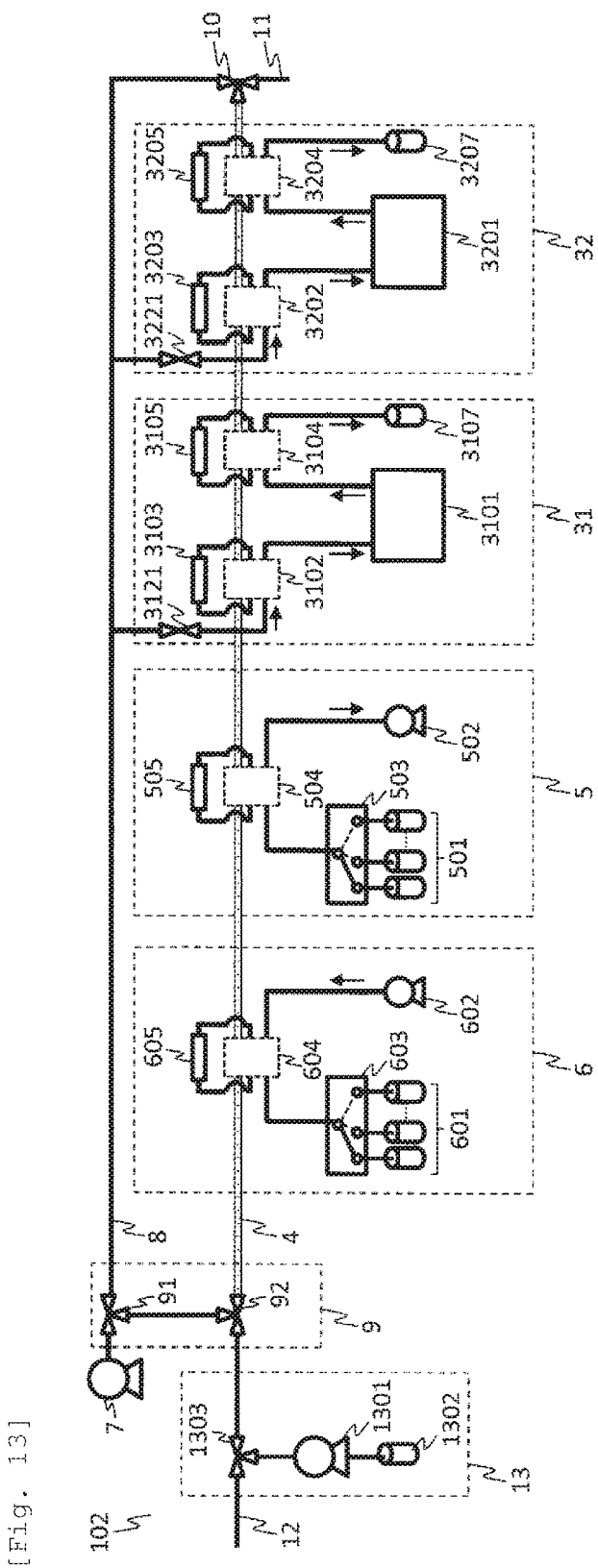
[Fig. 13]

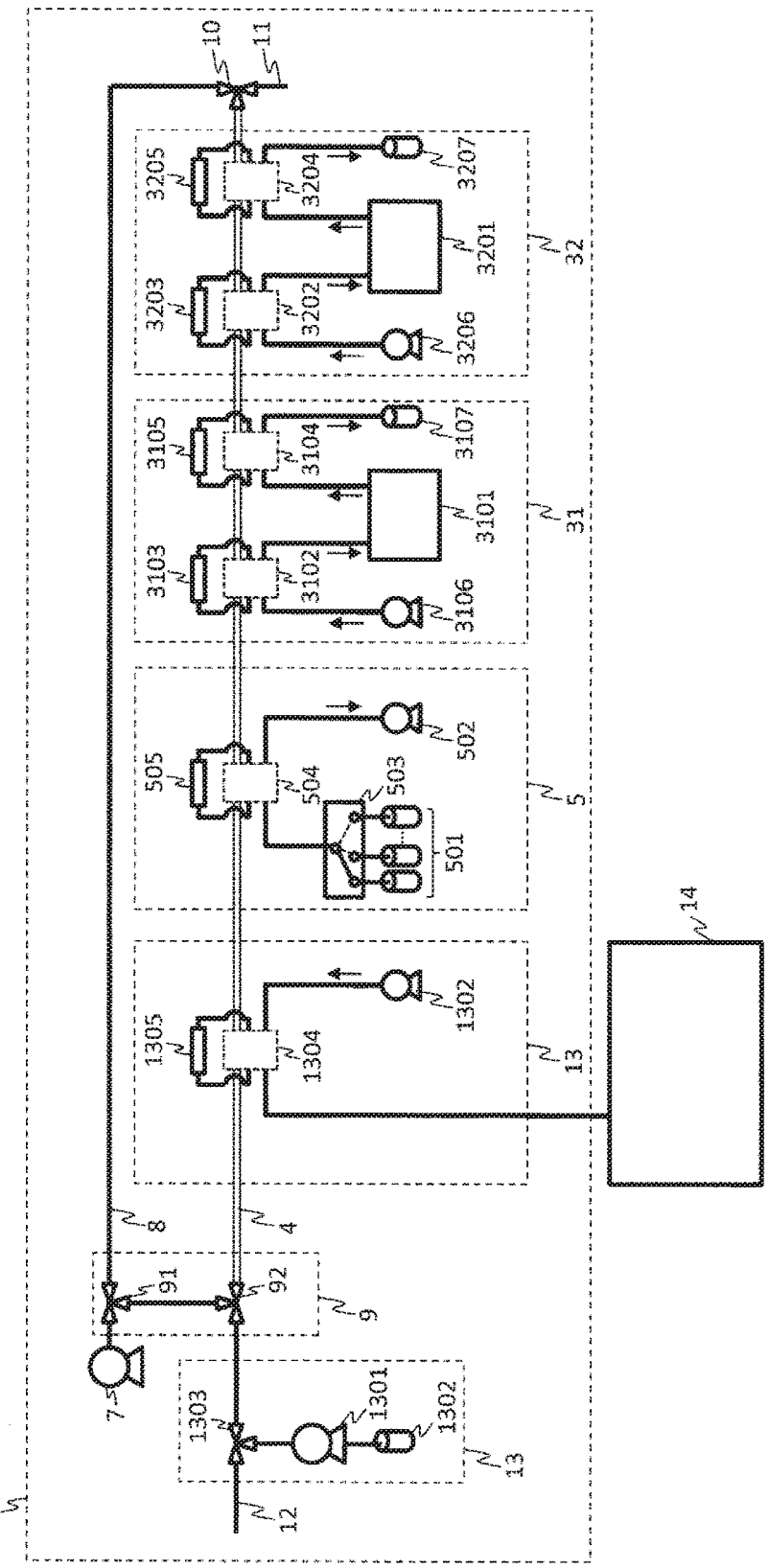
[Fig. 14]

PRETREATMENT DEVICE FOR SAMPLE FOR ANALYSIS, AND ANALYSIS SYSTEM USING SAME

TECHNICAL FIELD

The present invention relates to a pretreatment device that carries out pretreatment on a sample liquid which is an analysis target and, particularly, to a pretreatment device for a sample and an analysis system in chemical analysis.

BACKGROUND ART

In general, a pretreatment device for a sample in chemical analysis is configured of combination of a plurality of modules that carry out processes of pretreatment. The processes of the pretreatment include, for example, a process of adding and mixing a reagent to a sample, a process of heating a sample liquid to which the reagent is added, and the like. As an analysis device including such a pretreatment device, a device disclosed in PTL 1 has been known.

In PTL 1, there are provided, in a first flow path from the upstream side, a first sample introducing unit for mixing a sample and a reagent, a pretreatment unit that carries out thermolysis of a reagent-mixed sample liquid in a constant-temperature oven, a second sample introducing unit that introduces the sample liquid obtained after the thermolysis and causes the sample liquid to flow in a loop having a length of a flow path which varies depending on concentration of the sample. Further, a coloring unit that introduces the sample liquid from the second sample introducing unit through a second flow path and adds a coloring reagent thereto, and a detection unit that detects the sample liquid to which the coloring reagent is added are included.

CITATION LIST

Patent Literature

PTL 1: JP-A-9-218204

SUMMARY OF INVENTION

Technical Problem

In a configuration of PTL 1, a mixture, to which a sample liquid or a reagent is added, is caused to flow only in one direction from the upstream side to the downstream side of the first flow path. Therefore, in a case where a pretreatment process of adding another reagent, or the like, to the sample liquid obtained after the thermolysis by the pretreatment unit is needed, a new treatment unit has to be provided on the downstream side of the pretreatment unit in the first flow path.

This is because PTL 1 does not include a configuration of switching a flow path which introduces the sample liquid to the first flow path from a treatment module such as the first sample introducing unit, the pretreatment unit, the second sample introducing unit, or the like. Therefore, in a configuration as in PTL 1, it is not possible to carry out pretreatment of a multi-stage process in a treatment module which is disposed at an arbitrary position, using a plurality of treatment modules connected to the first flow path.

The present invention provides a pretreatment device for a sample for analysis that makes it possible to send a sample liquid to an arbitrary treatment module connected to a sample liquid conveyance flow path, and an analysis system using the same.

Solution to Problem

In order to solve the above problem, a pretreatment device for a sample for analysis of the present invention includes, at least: a plurality of sample liquid treatment modules for introducing a sample liquid or carrying out prescribed pretreatment on the sample liquid; a first flow path for conveying the sample liquid or the pretreated sample liquid between the plurality of sample liquid treatment modules; and a conveyance direction switching part for switching the conveyance direction of the sample liquid or the pretreated sample liquid in the first flow path. The sample liquid treatment module has an introduction flow path for introducing the sample liquid or the pretreated sample liquid from the first flow path, a discharge flow path for sending the sample liquid or the pretreated sample liquid to the first flow path, and a flow path switching part for switching the state of communication with the first flow path of the introduction flow path and the discharge flow path.

In addition, an analysis system of the present invention includes: (1) a pretreatment device including, at least a plurality of sample liquid treatment modules for introducing a sample liquid or carrying out prescribed pretreatment on the sample liquid, a first flow path for conveying the sample liquid or the pretreated sample liquid between the plurality of sample liquid treatment modules, and a conveyance direction switching part for switching the conveyance direction of the sample liquid or the pretreated sample liquid in the first flow path, in which the sample liquid treatment module has an introduction flow path for introducing the sample liquid or the pretreated sample liquid from the first flow path, a discharge flow path for sending the sample liquid or the pretreated sample liquid to the first flow path, and a flow path switching part for switching the state of communication with the first flow path of the introduction flow path and the discharge flow path; and (2) an analysis device that introduces the pretreated sample liquid from the pretreatment device and performs prescribed analysis.

Advantageous Effects of Invention

According to the present invention, it is possible to send a liquid to an arbitrary module connected to a sample liquid conveyance flow path, and thus, it is possible to provide a pretreatment device and an analysis system using the same in which it is possible to reduce the pretreatment device in size.

For example, it is possible to treat, in a module provided on the upstream side, the sample liquid treated by another module provided on the downstream side of the sample liquid conveyance flow path, and thus, it is possible to achieve feature expansion of the pretreatment apparatus or to carry out treatment in respective modules in an arbitrary order.

Other problems, configurations, and effects which are not described above will become clear in the following description of embodiments.

BRIEF DESCRIPTION OF DRAWINGS

FIG. 1 is a view illustrating an overall configuration of a pretreatment device according to an example of the present invention.

FIG. 2 is a flowchart of treatment carried out by the pretreatment device illustrated in FIG. 1.

FIG. 5C is a view illustrating still another schematic configuration of a detection unit that detects filling with a sample liquid into a buffer in the sample liquid introduction module.

FIG. 7 is a view illustrating an operation state by a first sample liquid treatment module illustrated in FIG. 1.

FIG. 8 is a view illustrating another operation state by the first sample liquid treatment module illustrated in FIG. 1.

FIG. 9 is a view illustrating an operation state by a second sample liquid treatment module illustrated in FIG. 1.

FIG. 10 is a view illustrating another operation state by the second sample liquid treatment module illustrated in FIG. 1.

FIG. 11 is a view illustrating still another operation state by the first sample liquid treatment module illustrated in FIG. 1.

FIG. 13 is a view illustrating an overall configuration of a pretreatment device according to another example of the present invention.

FIG. 14 is a view illustrating an overall configuration of an analysis system including the pretreatment device according to the example of the present invention.

DESCRIPTION OF EMBODIMENTS

Figure 3A:
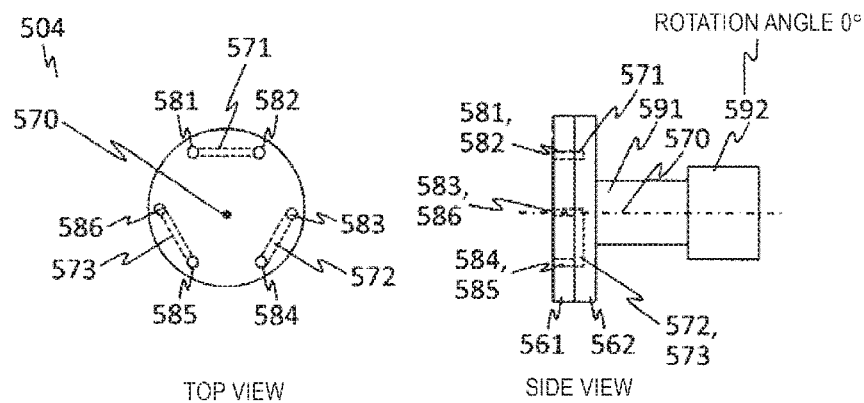
FIG. 3A is a view illustrating an operation state of a flow path switching part illustrated in FIG. 1.

Hereinafter, examples of the present invention will be described with reference to the drawings.

Example 1

In the present example, an example of a pretreatment device 101 for carrying out pretreatment on a sample in chemical analysis will be described. FIG. 1 is a view illustrating an overall configuration of the pretreatment device 101 according to the example of the present invention. The pretreatment device 101 is configured to include a first sample liquid treatment module 31 for carrying out treatment on a sample liquid which is a target of pretreatment, a second sample liquid treatment module 32, a sample liquid introduction module 5 for introducing the sample liquid, a sample liquid conditioning module 6 for conditioning the pretreated sample, and a sample liquid conveyance flow path 4 as a first flow path for conveying the sample liquid between the modules.

In addition, the pretreatment device 101 further includes a compressor 7 for supplying compressed air so as to extrude the sample liquid in the sample liquid conveyance flow path 4, a compressed air flow path 8 as a second flow path for injecting the compressed air from the compressor 7 into the sample liquid conveyance flow path 4, a compressed air direction switching part 9 for switching a conveyance direction of the sample liquid flowing in the sample liquid conveyance flow path 4, and a cleaning part 13 for cleaning a three-way valve 10 provided at one end of the sample liquid conveyance flow path 4 and the inside of the sample liquid conveyance flow path 4. The three-way valve 10 allows one end of the sample liquid conveyance flow path 4 to communicate with one of the compressed air flow path 8 or an open end 11. In addition, an open end 12 is provided in a flow path which can be connected to the sample liquid conveyance flow path 4 through the compressed air direction switching part 9, on the upstream side of the cleaning part 13.

The first sample liquid, treatment module 31 includes a sample liquid treating unit 301 for carrying out treatment on the sample liquid, a switching unit 3102 for introducing the sample liquid that introduces the sample liquid to the sample liquid treating unit 3101 from the sample liquid conveyance flow path 4, a sample liquid introducing buffer 3103 for temporarily accumulating the sample liquid when the sample liquid is introduced to the sample liquid treating unit 3101 from the sample liquid conveyance flow path 4, a switching unit 3104 for discharging the sample liquid that discharges the sample liquid to the sample liquid conveyance flow path 4 from the sample liquid treating unit 3101, a sample liquid discharging buffer 3105 for temporarily accumulating the sample liquid when the sample liquid is discharged to the sample liquid conveyance flow path 4 from the sample liquid treating unit 3101, a sample liquid sending pump 3106 for sending the sample liquid in the sample liquid treating unit 3101, a drainage conditioning vessel 3107 for conditioning drainage from the sample liquid treating unit 3101, and piping for connecting the members.

Since the second sample liquid treatment module 32 has the same configuration as the first sample liquid treatment module 31, description thereof is omitted.

The sample liquid introduction module 5 includes a pretreatment-target sample liquid vessel 501 for conditioning a pretreatment-target sample liquid, a sample liquid introducing pump 502 for suctioning the sample liquid from the pretreatment-target sample liquid vessel 501, a selection valve 503 for introducing the sample liquid that selects one of a plurality of pretreatment-target sample liquid vessels and connects the selected vessel to the sample liquid introducing pump 502, a switching unit 504 for introducing the sample liquid that introduces the sample liquid to the sample liquid conveyance flow path 4 from the pretreatment-target sample liquid vessel 501, and a sample liquid introducing buffer 505 for temporarily accumulating the sample liquid when the sample liquid is introduced to the sample liquid conveyance flow path 4 from the pretreatment-target sample liquid vessel 501.

The sample liquid conditioning module 6 includes a pretreated sample liquid vessel 601 for conditioning a pretreated sample liquid, a sample liquid conditioning pump 602 for sending the pretreated sample liquid to the pretreated sample liquid vessel 601, a selection valve 603 for conditioning the sample liquid that selects one of a plurality of pretreated sample liquid vessels and connects the selected vessel to the sample liquid conditioning pump 602, a switching unit 604 for conditioning the sample liquid for discharging the sample liquid to the pretreated sample liquid vessel 601 from the sample liquid conveyance flow path 4, and a sample liquid conditioning buffer 605 for temporarily accumulating the pretreated sample liquid when the pretreated sample liquid is discharged to the pretreated sample liquid vessel 601 from the sample liquid conveyance flow path 4.

The compressed air direction switching part 9 includes a three-way valve 91 and a three-way valve 92. The three-way valve 92 allows an end portion of the sample liquid conveyance flow path 4 to communicate with one of the cleaning part 13 or the three-way valve 91. In addition, the three-way valve 91 allows an end portion of the compressed air flow path 8 as the second flow path to communicate with one of the compressor 7 or the three-way valve 92.

The cleaning part 13 includes a cleaning liquid sending pump 1301 for sending a cleaning liquid, a cleaning liquid conditioning vessel 1302 for conditioning the cleaning liquid, and a three-way valve 1303. The three-way valve 1303 allows the cleaning liquid to communicate with the three-way valve 92 in the compressed air direction switching part 9 or allows the three-way valve 92 to communicate with the open end 12. Here, the cleaning liquid is, for example, an alkaline chemical agent and performs cleaning by causing the protein contained in the sample liquid attached on a wall surface in a flow path such as the sample liquid conveyance flow path 4 to be dissolved.

Hereinafter, a case in which derivatization treatment of an amino acid sample is performed using the pretreatment device 101 will be described as an example. There is a method in which an NBD-F derivatization sample is used as an example of derivatization of the amino acid sample. Specific treatment processes of the method are as follows.

(a) Weighing of sample liquid (liquid containing amino acid)
(b) Mixing first reagent R1 (NBD-F reagent) with sample liquid
(c) Mixing second reagent R2 (buffer solution) with sample liquid
(d) derivatized by heating
(e) Mixing third reagent R3 (neutralizing solution) with sample liquid FIG. 2 illustrates a flowchart of treatment formed in a case where the treatment processes described above is realized in the pretreatment device 101 of the present example illustrated in FIG. 1.

An intended sample liquid is conveyed to the first sample liquid treatment module 31 by the sample liquid introduction module 5 (Step S101).

The first sample liquid treatment module 31 performs adding and mixing of the first reagent R1 and the second reagent R2 to the sample liquid conveyed through the sample liquid conveyance flow path 4 as the first flow path (Step S102). Steps S101 and S102 correspond to the above treatment processes (a), (b), and (c). In addition, at the same time as Step S102, the cleaning liquid is caused to flow into the sample liquid conveyance flow path 4 from the cleaning part 13 (Step S103) and the cleaning liquid is discharged after cleaning the sample liquid conveyance flow path 4 (Step S104).

Next, the first sample liquid treatment module 31 causes a mixture of the first reagent R1 and the second reagent R2 with the sample liquid to be sent to the second sample liquid treatment module 32 through the sample liquid conveyance flow path 4 (Step S105). At the same time as Step S105, the cleaning liquid from the cleaning part 13 is supplied to the first sample liquid treatment module 31 through the sample conveyance flow path 4, and performs cleaning of a flow path in the first sample liquid treatment module 31 (Step S106). The cleaning liquid is discharged after the cleaning (Step S107).

The second sample liquid treatment module 32 heats, for a predetermined period of time, the mixture of the first reagent R1 and the second reagent R2 with the sample liquid conveyed through the sample liquid conveyance flow path 4 (Step S108). Step S108 corresponds to the above treatment process (d). At the same time as Step S108, the cleaning liquid is caused to flow into the sample liquid conveyance flow path 4 from the cleaning part 13 (Step S109) and the cleaning liquid is discharged after cleaning the sample liquid conveyance flow path 4 (Step S110).

Subsequently, the second sample liquid treatment module 32 causes the heated mixture of the first reagent R1 and the second reagent R2 with the sample liquid for the predetermined period of time to be conveyed to the first sample liquid treatment module 31 through the sample liquid conveyance flow path 4 (Step S111). At the same time as Step S111, the cleaning liquid from the cleaning part 13 is supplied to the second sample liquid treatment module 32, and performs cleaning of a flow path in the second sample liquid treatment module 32 (Step S112). The cleaning liquid is discharged after the cleaning (Step S113).

The first sample liquid treatment module 31 performs adding and mixing of the third reagent R3 to the heated mixture of the first reagent R1 and the second reagent R2 with the sample liquid for the predetermined period of time, which is conveyed through the sample liquid conveyance flow path 4 (Step S114). Step S114 corresponds to the above treatment process (e). At the same time as Step S114, the cleaning liquid is caused to flow into the sample liquid conveyance flow path 4 from the cleaning part 13 (Step S115) and the cleaning liquid is discharged after cleaning the sample liquid conveyance flow path 4 (Step S116).

Subsequently, the first sample liquid treatment module 31 causes the mixture to which the third reagent R3 is added, that is, the pretreated sample liquid to be conveyed to the pretreated sample liquid conditioning module 6 through the sample liquid conveyance flow path 4 (Step S117). At the same time as Step S117, the cleaning liquid from the cleaning part 13 is supplied to the first sample liquid treatment module 31, and performs cleaning of the flow path in the first sample liquid treatment module 31 (Step S118). The cleaning liquid is discharged after the cleaning (Step S119). The derivatization of the amino acid sample as the pretreatment is ended.

Figure 3B:
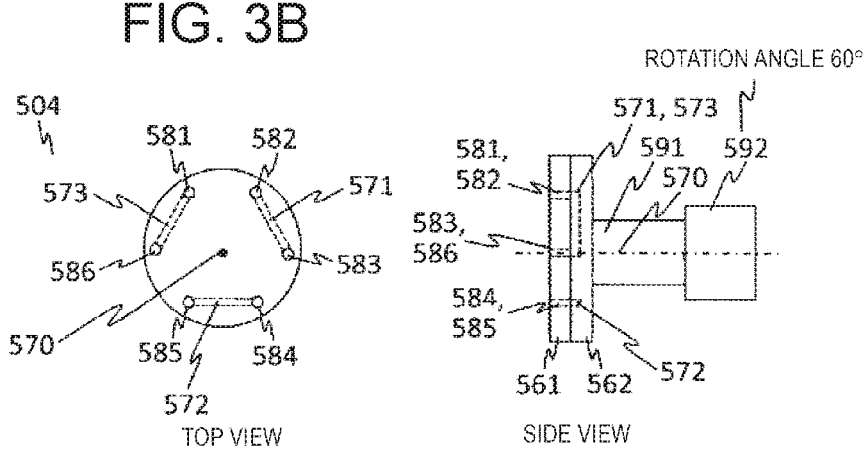
FIG. 3B is a view illustrating another operation state of the flow path switching part illustrated in FIG. 1.

Here, a configuration of the switching unit 501 for introducing the sample liquid in the sample liquid introduction module 5 illustrated in FIG. 1 will be described. FIGS. 3(a) and 3(b) illustrate operational states of the switching unit 504 for introducing the sample liquid.

As illustrated in the top view and the side view in 3(a), the switching unit 504 for introducing the sample liquid includes a stator 561 having six connection ports 581, 582, 583, 584, 585, and 586 which are formed in a penetration opening, a rotor 562 in which there are formed three internal flow paths 571, 572 and 573 having openings at both end portions thereof on a surface facing the rear surface of the stator 561, and a motor 592 that is connected to the rear surface of the rotor 562 through a rotary shaft 591. The switching unit 504 for introducing the sample liquid has a configuration in which the motor 592 drives and rotates the rotor 562 about a central axis 570 with respect to the stator 561, thereby making it possible to switch connecting relationships between the six connection ports 581, 582, 583, 584, 585, and 586 formed in the stator 561 and three internal flow paths 571, 572 and 573 formed in the rotor 562. The switching unit for introducing the sample liquid functions as a six-way valve.

In a state illustrated in FIG. 3(a), the connection port 581 communicates with the connection port 582 through the internal flow path 571, the connection port 583 communicates with the connection port 584 through the internal flow path 572, and the connection port 585 communicates with the connection port 586 through the internal flow path 573. FIG. 3(b) illustrates a state in which the rotor 562 rotates clockwise in a radial direction by 60° toward the stator 561 with respect to the stator 561, from the state in FIG. 3(a). As illustrated in FIG. 3(b), the connection port 582 communicates with the connection port 583 through the internal flow path 571, the connection port 584 communicates with the connection port 585 through the internal flow path 572, and the connection port 581 communicates with the connection port 586 through the internal flow path 573.

As above, the six-way valve can switch a state of communication with the six connection ports into two patterns in the inside thereof. Hereinafter, the state of communication illustrated in FIG. 3(a) is referred to as a pattern A and the state of communication illustrated in FIG. 3(b) is referred to as a pattern B.

Configurations of the switching unit 3102 for introducing the sample liquid, the switching unit 3104 for discharging the sample liquid, a switching unit 3202 for introducing the sample liquid, a switching unit 3204 for discharging the sample liquid, and the switching unit 604 for conditioning the sample liquid illustrated in FIG. 1 are the same as the configuration of the switching unit 504 for introducing the sample liquid. In the present example, a configuration in which the switching units function as the six-way valve is described; however, the example is not limited thereto, it is possible to be realized by combining a plurality of three-way valves or two-way valves.

In addition, in an initial state of the pretreatment device 101, the switching unit 3102 for introducing the sample liquid is switched to a position at which a connection port 3181 and a connection port. 3182, a connection port 3183 and a connection port 3184, and a connection port 3185 and a connection port 3186 communicate with each other in the switching unit 3102 for introducing the sample liquid (a state of communication of the pattern A described above). The switching unit 3104 for discharging the sample liquid, the switching unit 3202 for introducing the sample liquid, the switching unit 3204 for discharging the sample liquid, the switching unit 504 for introducing the sample liquid, and the switching unit 604 for conditioning the sample liquid are switched to the same position as the switching unit 3102 for introducing the sample liquid (a state of communication of the pattern A described above).

As above, in the initial state of the pretreatment device 101, the switching units in all of the modules provided in the sample liquid conveyance flow path 4 as the first flow path, that is, all of the switching unit 3102 for introducing the sample liquid and the switching unit 3104 for discharging the sample liquid in the first sample liquid treatment module 31, the switching unit 3202 for introducing the sample liquid and the switching unit 3204 for discharging the sample liquid in the second sample liquid treatment module 32, the switching unit 504 for introducing the sample liquid in the sample liquid introduction module 5, and the switching unit 604 for conditioning the sample liquid in the sample liquid conditioning module 6 are in the switched state of the pattern A in which a state of communication with the sample liquid conveyance flow path 4 is achieved.

Hereinafter, operational states of the modules will be described, respectively.

(1) Operation of Sample Liquid introduction Module 5

Figure 4A:
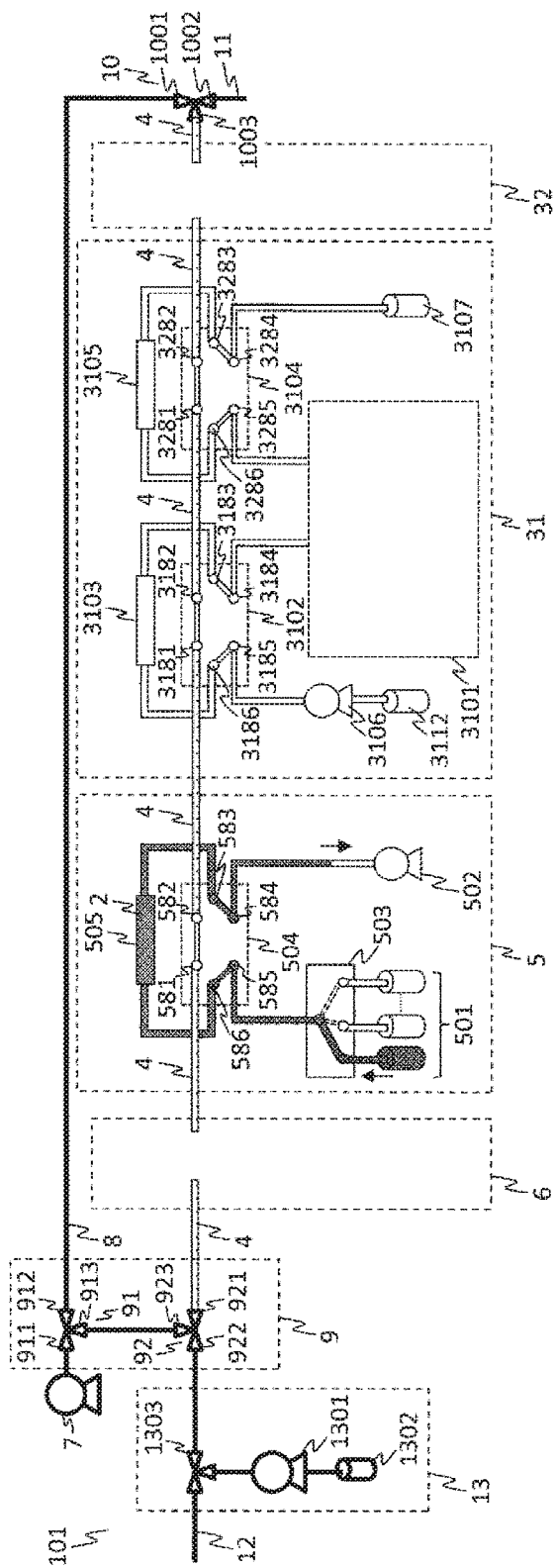
FIG. 4A is a view illustrating an operation state by a sample liquid introduction module illustrated in FIG. 1.
Figure 4B:
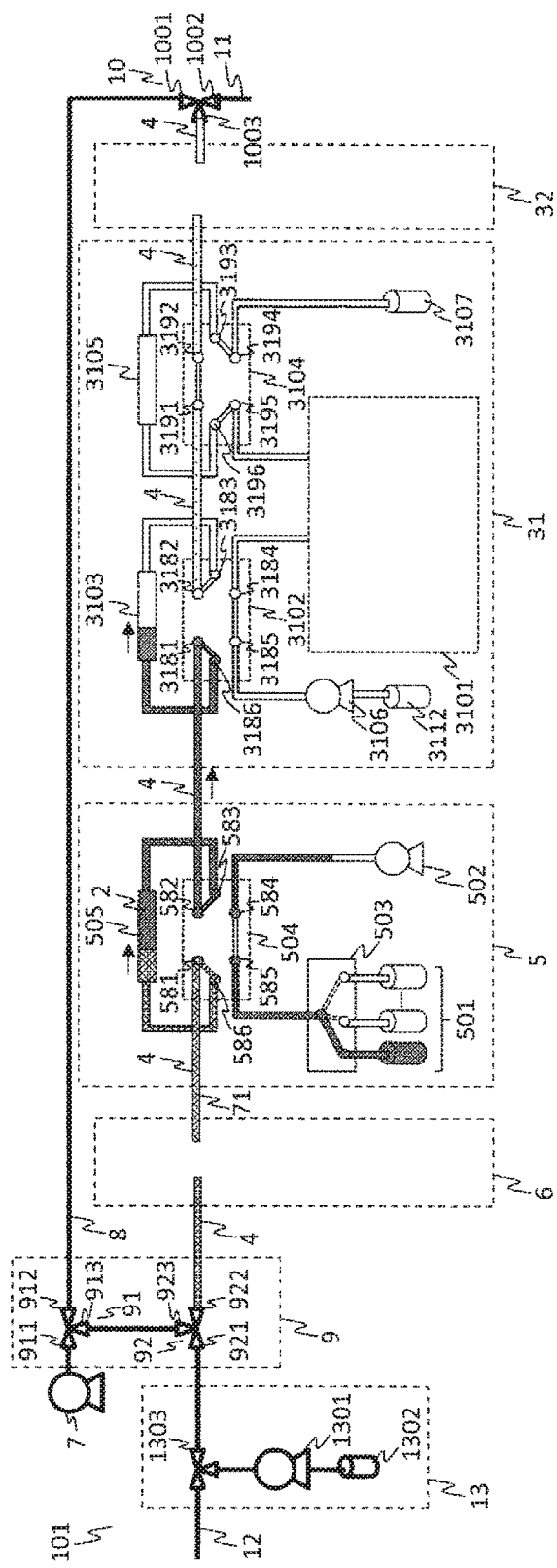
FIG. 4B is a view illustrating another operation state by a sample liquid introduction module illustrated in FIG. 1.

FIGS. 4(a) and 4(b) illustrate operational state of the sample liquid introduction module 5 illustrated in FIG. 1. The operational states in FIGS. 4(a) and 4(b) correspond to Step S101 illustrated in FIG. 2 described above.

First, as illustrated in FIG. 4(a), the switching unit 504 for introducing the sample liquid is switched to the state of communication of the pattern A. In other words, the switching is performed such that the connection port 581 and the connection port 582, the connection port 583 and the connection port 584, and the connection port 585 and the connection port 586 communicate to each other, respectively, in the switching unit 504 for introducing the sample liquid. In addition, the selection valve 503 for introducing the sample liquid is switched such that a sample liquid 2 entering the predetermined pretreatment-target sample liquid vessel 501 can be introduced into the sample liquid introducing buffer 505. In this state, the sample liquid introducing pump 502 performs suction, thereby filling the sample liquid introducing buffer 505 with the sample liquid 2.

Figure 5A:
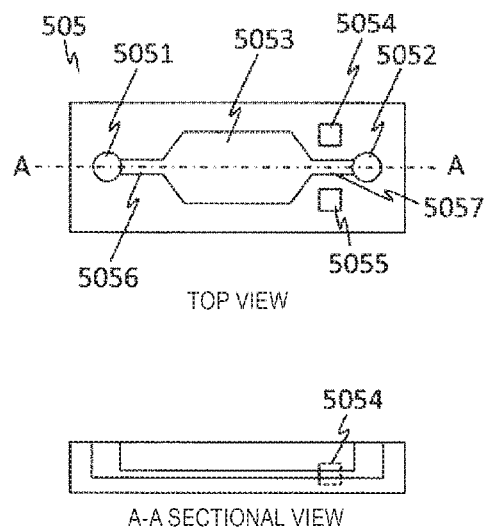
FIG. 5A is a view illustrating a schematic configuration of a detection unit that detects filling with a sample liquid into a buffer in the sample liquid introduction module.

Here, detection of completion of the filling the sample liquid introducing buffer 505 with the sample liquid 2 is described. FIG. 5(a) illustrates a configuration in which the completion of the filling with the sample liquid 2 is detected by using a light sensor. As illustrated in the top view in FIG. 5(a), in the sample liquid introducing buffer 505, a region 5053 in which a flow path has a widened width so as to temporarily accumulate the sample liquid 2, a flow path 5056 that connects an introduction port 5051 and the region 5053, and a flow path 5057 that connects a discharge port 5052 and the region 5053 are formed between the introduction port 5051 through which the sample liquid 2 is introduced and the discharge port 5052. At positions facing to interpose the flow path 5057 therebetween, a light irradiator 5054 and a light sensor 5055 that receives irradiation light from the light irradiator 5054 and detects the sample liquid 2 reaching the flow path 5057 based on the amount of light received or absorbance. The light irradiator 5054 is disposed at a position at which it is possible to perform irradiation with light from a side of the flow path 5057 through which the sample liquid 2 from the region 5053 is caused to flow. As above, the light sensor 5055 detects a change in the amount of light received or absorbance, thereby making it possible to detect the completion of the filling of the sample liquid introducing buffer 505 with the sample liquid 2.

Figure 5B:
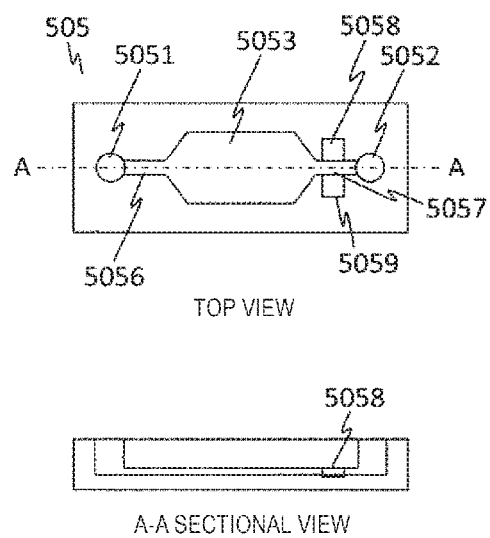
FIG. 5B is a view illustrating another schematic configuration of a detection unit that detects filling with a sample liquid into a buffer in the sample liquid introduction module.

In addition, FIG. 5(b) illustrates a configuration in which the completion of the filling is detected based on a potential difference. As illustrated in the top view and the A-A sectional view in FIG. 5(b), electrodes 5058 and 5059 are disposed on both sides of the flow path 5057. A potential difference between the electrodes is detected when the sample liquid 2 flows from the region 5053 and reaches the flow path 5057 in which the electrodes 5058 and 5059 described above are disposed, thereby making it possible to detect the completion of the filling of the sample liquid introducing buffer 505 with the sample liquid 2.

In addition, FIG. 5(c) illustrates a configuration in which the completion of the filling of the sample liquid introducing buffer 505 is detected based on detection of pressure. As illustrated in FIG. 5(c), an orifice 50511 that decreases a flow path width of the flow path 5056 is formed at a position at which the flow path 5056 is connected to the region 5053 or in the vicinity of the position, and, similarly, an orifice 50512 that decreases the width of the flow path is formed at a connection position between the region 5053 and the flow path 5057 or in the vicinity of the connection position. A pressure sensor 50513 that detects a pressure difference between the inside of the flow path 5056 and the inside of the flow path 5057 is provided. When the sample liquid 2 flows from, the region 5053 and reaches the orifice 50512, the pressure sensor 50513 detects a pressure loss through the orifice, thereby making it possible to detect the filling of the sample liquid introducing buffer 505 with the sample liquid 2.

Further, as a configuration of detecting the completion of the filling, in addition to the configurations described above, for example, a configuration, in which the completion of the filling of the sample liquid introducing buffer 505 is determined based on a period of time to be taken for the conveyance which is estimated depending on suction pressure of the sample liquid introducing pump 502 and a shape of the flow path (length of the flow path, a width of the flow path, and a sectional area of the flow path) through which the sample liquid 2 flows, may be employed. As described above, a configuration in which the completion of the filling is detected by any method described above may be employed. The sample liquid introducing pump 502 performs suction until the completion of the filling is detected by any method described above, and thereby, the sample liquid introducing buffer 505 is filled with the sample liquid 2.

Next, back to FIG. 4(b), the switching unit 504 for introducing the sample is switched to the state of communication of the pattern B described above. In other words, the switching is performed such that the connection port 581 and the connection port 586, the connection port 582 and the connection port 583, and the connection port 584 and the connection port 585 communicate to each other, respectively, in the switching unit 504 for introducing the sample liquid. Similarly, at this time, the switching unit 3102 for introducing the sample liquid in the first sample treatment module 31 is switched to the state of communication of the pattern B. In this manner, the switching is performed such that the connection port 3181 and the connection port 3186, the connection port 3182 and the connection port 3183, and the connection port 3184 and the connection port 3185 communicate with each other, respectively, in the switching unit 3102 for introducing the sample liquid.

In addition, the three-way valve 91, the three-way valve 92, and the three-way valve 10 are switched such that communication is performed in the following order, the compressor 7, the three-way valve 91, the three-way valve 92, the connection port 581, the connection port 586, the sample liquid introducing buffer 505, the connection port 583, the connection port 582, the connection port 3181, the connection port 3186, the sample liquid introducing buffer 3103, the connection port 3183, the connection port 3182, the three-way valve 10, and the open end 11. At this time, the state of communication of the pattern A is similarly maintained in the switching unit 3104 for discharging the sample quid in the first sample liquid treatment module 31, the switching unit 3202 for introducing the sample liquid and the switching unit 3204 for discharging the sample liquid, in the second sample liquid treatment module 32, thereby achieving a state of communicating the open end 11 through the sample liquid conveyance flow path 4.

In this state, compressed air 71 is supplied from the compressor 7, thereby, the sample liquid 2 in the sample liquid introducing buffer 505 is extruded from the sample liquid introducing buffer 505 and is conveyed to the sample liquid introducing buffer 3103 in the first sample liquid treatment module 31 through the sample liquid conveyance flow path 4, the connection port 3181, and the connection port 3186. At this time, the sample liquid 2 flows into the sample liquid introducing buffer 3103 and, thereby, air present in the sample liquid, introducing buffer 3103 until then is discharged through the open end 11.

A method of determining the completion of the filling of the sample liquid introducing buffer 3103 with the sample liquid 2 is performed in the same way as the detection of the completion of the filling of the sample liquid introducing buffer 505 with the sample liquid 2.

Next, in the operation state of the sample liquid introduction module 5 illustrated in FIGS. 4(a) and 4(b) described above, operational timing of a filling detection mechanism of the selection valve 503 for introducing the sample liquid, the switching unit 504 for introducing the sample liquid, the sample liquid introducing pump 502, and the sample liquid introducing buffer 505.

Figure 6A:
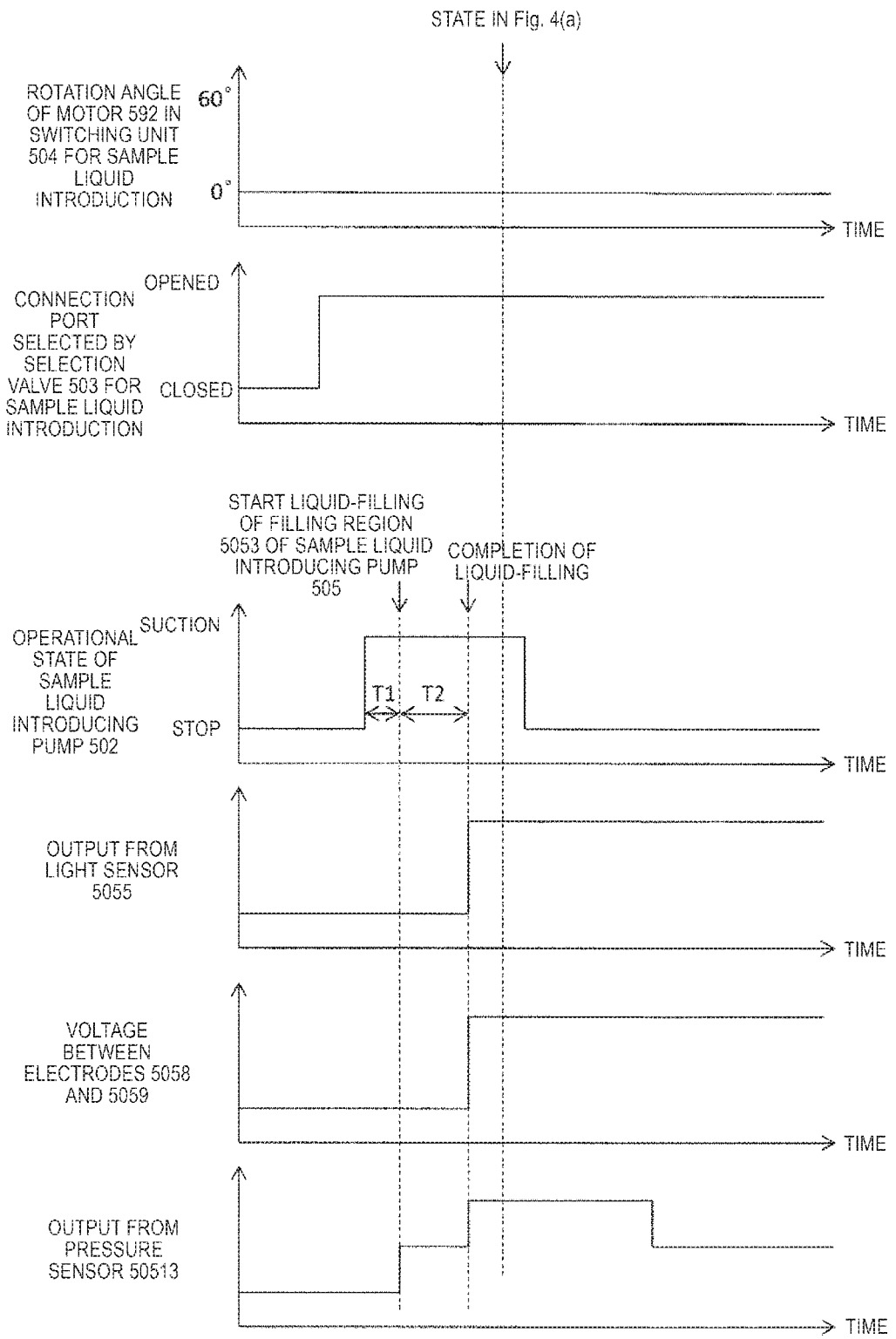
FIG. 6A is an operation timing chart of the flow path switching part and the detection unit detecting filling with sample liquid to the buffer.

FIG. 6(a) illustrates operational timing of the above members in the operational state of the sample liquid introduction module 5 illustrated in FIG. 4(a).

In the state in which the rotation angle of the motor 592 in the switching unit 504 for introducing the sample liquid illustrated in FIG. 3(a) is 0°, that is, when the state of communication is the pattern A, the switching is performed to an open state such that the connection port selected by the selection valve 503 for introducing the sample liquid is in a completely opened state and, thus, is connected to any pretreatment-target sample liquid vessels 501. Then, the sample liquid introducing pump 502 starts to operate in a suction state from the stop state. After a predetermined period of time (T1) elapses from the start of the suction state, the sample liquid 2 flows into the region 5053 describe above in the sample liquid introducing buffer 505, that is, the buffer 505 starts to be filled with the sample liquid 2.

When a predetermined period of time (T2) elapses after the start of the filling, the completion of the filling of the buffer 505 with the sample liquid 2 is detected based on an output from the light sensor 5055 illustrated in FIG. 5(a), the potential difference between the electrodes 5058 and 5059 illustrated in FIG. 5(b), and the pressure sensor 50513 illustrated in FIG. 5(c) and then, the sample liquid introducing pump 502 stops.

As illustrated in FIG. 6(a), in a method in which the completion of the filling with the sample liquid 2 is detected detecting a pressure loss by the pressure sensor 50513, when the sample liquid 2 reaches the orifice 50511, the width of the flow path is rapidly decreased and, thereby, the output is detected by the pressure sensor 50513. Then, when the sample liquid 2 from the region 5053 reaches the orifice 50512, a pressure loss is again detected.

Figure 6B:
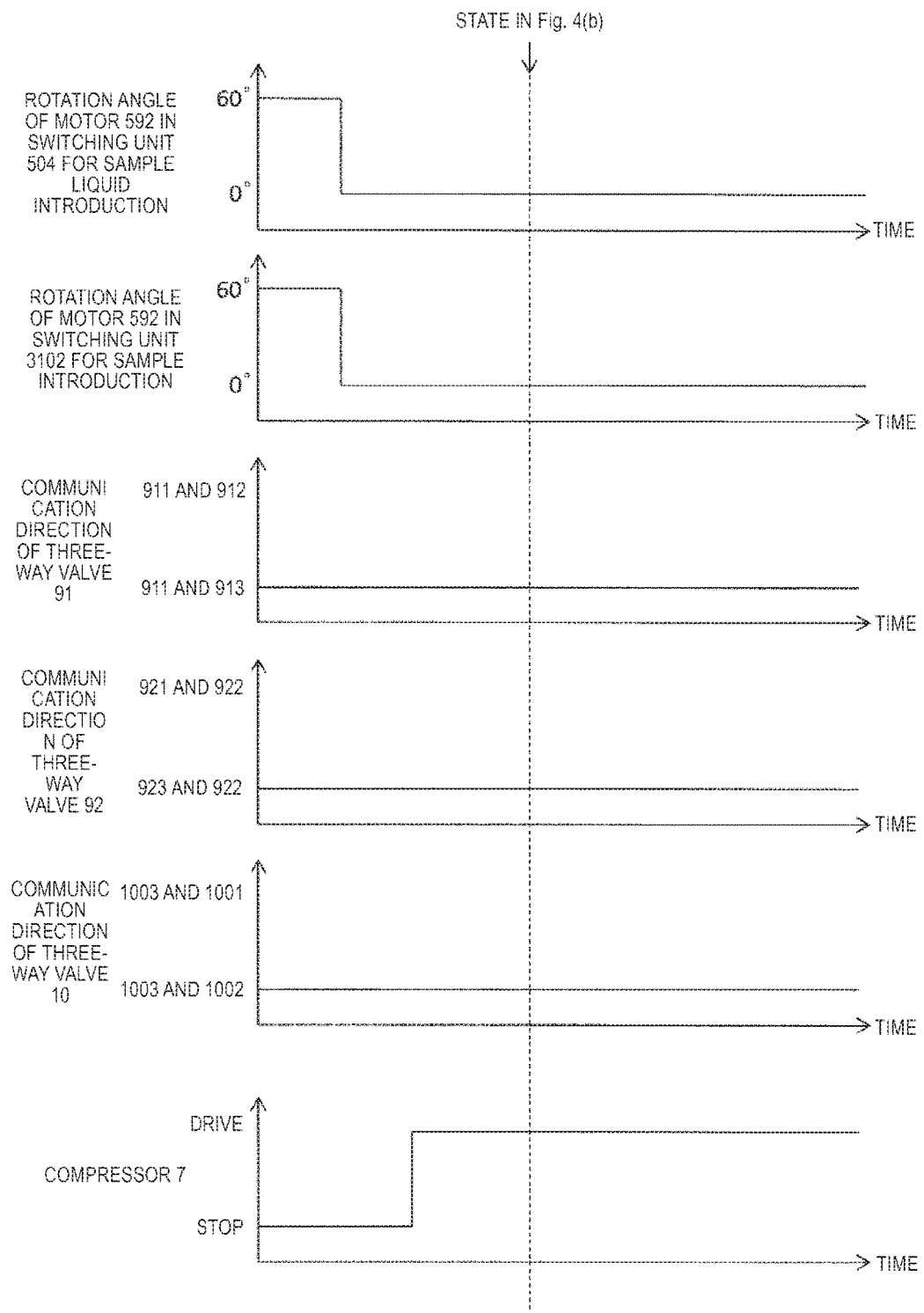
FIG. 6B is a timing chart of the flow path switching part and supplying of compressed air to the buffer.

FIG. 6(b) illustrates operational timing of the above members in the operational state of the sample liquid introduction module 5 illustrated in FIG. 4(b).

In FIG. 6(a), after the sample liquid introducing pump 502 stops, the motor 592 in the switching unit 504 for introducing the sample liquid drives and rotates the rotor in the radial direction by a rotation angle of 60°, in synchronization with the driving, the motor in the switching unit 3102 for introducing the sample liquid in the first sample liquid treatment module 31 drives and rotates the rotor in the radial direction by a rotation angle of 60°, and the state of communication becomes state of the pattern B described above.

In this state, control of the respective valves is performed such that the three-way valves 91 in the compressed air direction switching part 9 is in a state of communication with 911 and 913, the three-way valves 92 is in a state of communication with 923 and 922, and the three-way valves 10 is in a state of communication with 1003 and 1002. Then, the compressor 7 starts to operate and the compressed air 71 is supplied to the connection port 581, the connection port 586, and the sample liquid introducing buffer 505 through the sample liquid conveyance flow path 4.

As above, a sample liquid conveyance process in Step S101 in FIG. 2 described above is carried out (2) Operation of First Sample Liquid Treatment Module 31

FIGS. 7 and 8 illustrate operational states of the first sample liquid treatment module 31 illustrated in FIG. 1. FIG. 7 corresponds to Step S102 in FIG. 2 and FIG. 8 corresponds to Step S105 in FIG. 2.

Here, as illustrated in FIG. 7, the sample liquid treating unit 3101 in the first sample liquid treatment module 31 includes a mixing device 3108, a first reagent sending pump 3109, a second reagent sending pump 3110, a third reagent sending pump 3111, and piping connected to the members. As the mixing device 3108, it is possible to use a microfluidic device using a flow path which is formed on a substrate and has a width of hundreds of micrometers or less, or a configuration in which the piping is joined with a T joint. At this time, a prescribed mixing ratio of the sample liquid, the first reagent R1, and the second reagent R2 is realized based on a flow ratio of the sample liquid sending pump 3106, the first reagent sending pump 3109, and the second reagent sending pump 3110.

First, the switching unit 3102 for introducing the sample liquid is switched to the state of communication of the pattern A from the pattern B described above. In other words, the switching is performed such that the connection port 3181 and the connection port 3182, the connection port 3183 and the connection port 3184, and the connection port 3185 and the connection port 3186 communicate with each other, respectively, in the switching unit 3102 for introducing the sample liquid. In addition, the switching unit 3104 for discharging the sample liquid is in the state of maintaining the state of communication of the pattern A and a connection port 3191 and a connection port 3192, a connection port 3193 and a connection port 3194, and a connection port 3195 and a connection port 3196 communicate with each other, respectively, in the switching unit 3104 for discharging the sample liquid.

In this state, the system water 3112 is sent by the sample liquid sending pump 3106, thereby, the sample liquid 2 in the sample liquid introducing buffer 3103 is extruded by the system water 3112, and the sample liquid is sent into the mixing device 3108. Here, the system water 3112 is also referred to as a carrier liquid and, for example, pure water or the like is used. At the same time, the first reagent R1 is sent by the first reagent sending pump 3109 and the second reagent R2 is sent by the second reagent sending pump 3110 into the mixing device 3108, thereby mixing the sample liquid 2, the first reagent R1, and the second reagent R2 in the mixing device 3108.

A first reagent-second reagent-mixed sample liquid 202 as the mixture of the sample liquid 2, the first reagent R1, and the second reagent R2, passes through the sample liquid discharging buffer 3105 and is sent into the drainage conditioning vessel 3107. In this manner, the sample liquid discharging buffer 3105 is filled with the first reagent-second reagent-mixed sample liquid 202.

Here, as a method of determining the completion of the filling of the sample liquid discharging buffer 3105 with the first reagent-second reagent-mixed sample liquid 202, any one method illustrated in FIG. 5(*a*), 5(*b*), or 5(*c*) described above may be used.

As above, the treatment in Step S102 in FIG. 2 is ended.

Subsequently, as illustrated in FIG. 8, the switching unit 3104 for discharging the sample liquid is switched to the state of communication of the pattern B from the pattern A described above. In other words, the connection port 3191 and the connection port 3196, the connection port 3192 and the connection port 3193, and the connection port 3194 and the connection port 3195 communicate with each other, respectively, in the switching unit 3105 for discharging the sample liquid.

In addition, the switching unit 3202 for introducing the sample liquid in the second sample liquid treatment module 32 is switched to the state of communication of the pattern B from the pattern A. In other words, a connection port 3281 and a connection port 3286, a connection port 3282 and a connection port 3283, and a connection port 3284 and a connection port 3285 communicate with each other, respectively, in the switching unit 3202 for introducing the sample liquid.

In addition, the three-way valve 91, the three-way valve 92, and the three-way valve 10 are switched such that communication is performed in the following order, the compressor 7 the three-way valve 91, the three-way valve 92, the connection port 3191, the connection port 3196, the sample liquid discharging buffer 3105, the connection port 3193, the connection port 3192, the connection port 3281, the connection port 3286, a sample liquid introducing buffer 3203, the connection port 3283, the connection port 3282, the three-way valve 10, and the open end 11. In this state, the compressed air 71 is supplied from the compressor 7 and, thereby, the first reagent-second reagent-mixed sample liquid 202 in the sample liquid discharging buffer 3105 is conveyed into the sample liquid introducing buffer 3203. At this time, the first reagent-second reagent-mixed sample liquid 202 flows into the sample liquid introducing buffer 3203 and, thereby, air present in the buffer 3203 until then is discharged through the open end 11.

A method of determining the completion of the filling of the sample liquid introducing buffer 3203 with the first reagent-second reagent-mixed sample liquid 202 is the same as the method of determining the completion of the filling of the sample liquid introducing buffer 505 with the sample liquid 2 described above in FIGS. 5(*a*) to 5(*c*). In this manner, the treatment in Step S105 in FIG. 2 is ended.

(3) Operation of Second Sample Liquid Treatment Module 32

FIGS. 9 and 10 illustrate operational states of the second sample liquid treatment module 32 illustrated in FIG. 1. FIG. 9 corresponds to Step S108 in FIG. 2 and FIG. 10 corresponds to Step S111 in FIG. 2.

As illustrated in FIG. 9, the sample liquid treating unit 3201 in the second sample liquid treatment module 32 includes a flow path device 3208 in which a flow path 3211 is formed, a temperature control device 3209 that heats or cools the sample liquid in the flow path 3211, a temperature sensor 3210 that measures a temperature of the temperature control device 3209, and a control unit (not illustrated) that reads a value of the temperature sensor 3210 and controls the temperature control device 3209. As the temperature control device 3209, for example, a Peltier element, a ceramic heater, a refrigerant circulating machine, or the like, can be appropriately used. In addition, as the temperature sensor 3210, a thermocouple, a thermistor, a platinum resistor, or the like can be used. Control of the temperature of the temperature control device 3209 makes it possible to heat the sample liquid passing through the flow path 3211 to be heated to a predetermined temperature. In addition, a period of time for which the sample liquid 202 is accumulated in the flow path 3211 is controlled based on a flow rate of a sample liquid sending pump 3206, thereby making it possible to adjust the period of time to heat the sample liquid. Otherwise, when the flow path 3211 is filled with the sample liquid, the sample liquid sending pump 3206 temporarily stops sending and the sample liquid sending pump 3206 is again driven after a predetermined time elapses, thereby making it possible to discharge the sample liquid from the flow path 3211 and to adjust the period of time to heat the sample liquid.

First, the switching unit 3202 for introducing the sample liquid is switched to the state of communication of the pattern A from the pattern B. In other words, the switching is performed such that the connection port 3281 and the connection port 3282, the connection port 3283 and the connection port 3284, and the connection port 3285 and the connection port 3286 communicate with each other, respectively, the switching unit 3202 for introducing the sample liquid. In addition, the switching unit 3204 for discharging the sample liquid is in the state of maintaining the state of communication of the pattern A and a connection port 3291 and a connection port 3292, a connection port 3293 and a connection port 3294, and a connection port 3295 and a connection port 3296 communicate with each other, respectively, in the switching unit 3204 for discharging the sample liquid.

In this state, system water 3212 is sent by the sample liquid sending pump 3206, thereby, the first reagent-second reagent-mixed sample liquid 202 in the sample liquid introducing buffer 3203 is extruded by the system water 3212, and the sample liquid is sent into the flow path device 3208. In this manner, the first reagent-second reagent-mixed sample liquid 202 is heated by the temperature control device 3209 while passing through the flow path 3211. A heated sample liquid 203 as a sample liquid obtained by heating the first reagent-second reagent-mixed sample liquid 202 by the temperature control device 3209 passes through the sample liquid discharging buffer 3205 and the heated sample liquid is sent into the drainage conditioning vessel 3207. In this manner, the sample liquid discharging buffer 3205 is filled with the heated sample liquid 203.

A method of determining the completion of the filling of the sample liquid discharging buffer 3205 with the heated sample liquid 203 is the same as the method of determining the completion of the filling of the sample liquid introducing buffer 505 with the sample liquid 2 described in FIGS. 5(*a*) to 5(*c*). In this manner, the second sample liquid treatment module 32 operates and, thereby, the treatment in Step S108 in FIG. 2 is carried out.

Next, as illustrated in FIG. 10, the switching unit 3204 for discharging the sample liquid is switched to the state of communication of the pattern B from the pattern A. In other words, the connection port 3291 and the connection port 3296, the connection port 3292 and the connection port 3293, and the connection port 3294 and the connection port 3295 communicate with each other, respectively, in the switching unit 3204 for discharging the sample liquid. In addition, the switching unit 3102 for introducing the sample liquid, is switched such that the connection port 3181 and the connection port 3186, the connection port 3182 and the connection port 3183, and the connection port 3184 and the connection port 3185 communicate with each other, respectively, in the switching unit 3202 for introducing the sample liquid.

In addition, the three-way valve 91, the three-way valve 92, and the three-way valve 10 are switched such that communication is performed in the following order, the compressor 7, the three-way valve 91, the three-way valve 10, the connection port 3292, the connection port 3293, the sample liquid discharging buffer 3205, the connection port 3296, the connection port 3291, the sample liquid conveyance flow path 4, the connection port 3182, the connection port 3183, the sample liquid introducing buffer 3103, the connection port 3186, the connection port 3181, the three-way valve 92, the cleaning part 13, and the open end 12. In this state, the compressed air 71 is supplied from the compressor 7 and, thereby, the heated sample liquid 203 in the sample liquid discharging buffer 3205 is conveyed into the sample liquid introducing buffer 3103. At this time, the heated sample liquid 203 flows into the sample liquid introducing buffer 3103 and, thereby, air present in the sample liquid introducing buffer 3103 until then is discharged through the open end 12.

A method of determining the completion of the filling of the sample liquid introducing buffer 3103 with the heated sample liquid 203 is the same as the method of determining the completion of the filling of the sample liquid introducing buffer 505 with the sample liquid 2 described in FIGS. 5(*a*) to 5(*c*). In this manner, the second sample liquid treatment module 32 operates and, thereby, the treatment in Step S111 in FIG. 2 is carried out.

(4) Operation of First Sample Liquid Treatment Module 31

FIG. 11 illustrates an operational state of the first sample liquid treatment module 31. FIG. 11 corresponds to Step S114 in FIG. 2.

As illustrated in FIG. 11, the switching unit 3102 for introducing the sample liquid in the first sample liquid treatment module 31 is switched to the state of communication of the pattern A from the pattern B. In other words, the switching is performed such that the connection port 3181 and the connection port 3182, the connection port 3183 and the connection port 3184, and the connection port 3185 and the connection port 3186 communicate with each other, respectively, in the switching unit 3102 for introducing the sample liquid. In addition, the switching unit 3104 for discharging the sample liquid is in the state of maintaining the state of communication of the pattern. A and the connection port 3191 and the connection port 3192, the connection port 3193 and the connection port 3194, and the connection port 3195 and the connection port 3196 communicate with each other, respectively, in the switching unit 3104 for discharging the sample liquid.

In this state, the system water 3112 is sent by the sample liquid sending pump 3106, thereby, the heated sample liquid 203 in the sample liquid introducing buffer 3103 is extruded by the system water 3112, and the heated sample liquid is sent into the mixing device 3108. At the same time, the third reagent R3 is sent by the third reagent sending pump 3111 into the mixing device 3108, thereby mixing the heated sample liquid 203 with the third reagent R3 in the mixing device 3108.

A third reagent-mixed sample liquid 204 as the mixture of the heated sample liquid 203 with the third reagent R3 passes through the sample liquid discharging buffer 3105 and is sent into the drainage conditioning vessel 3107. In this manner, the sample liquid discharging buffer 3105 is filled with the third reagent-mixed sample liquid 204.

A method of determining the completion of the filling of the sample liquid discharging buffer 3105 with the third reagent-mixed sample liquid 204 is the same as the method of determining the completion of the filling of the sample liquid introducing buffer 505 with the sample liquid 2 described in FIGS. 5(*a*) to 5(*c*). In this manner, the first sample liquid treatment module 31 operates and, thereby, the treatment in Step S114 in FIG. 2 is carried out.

(5) Operation of Pretreated Sample Liquid Conditioning Module 6

Figure 12A:
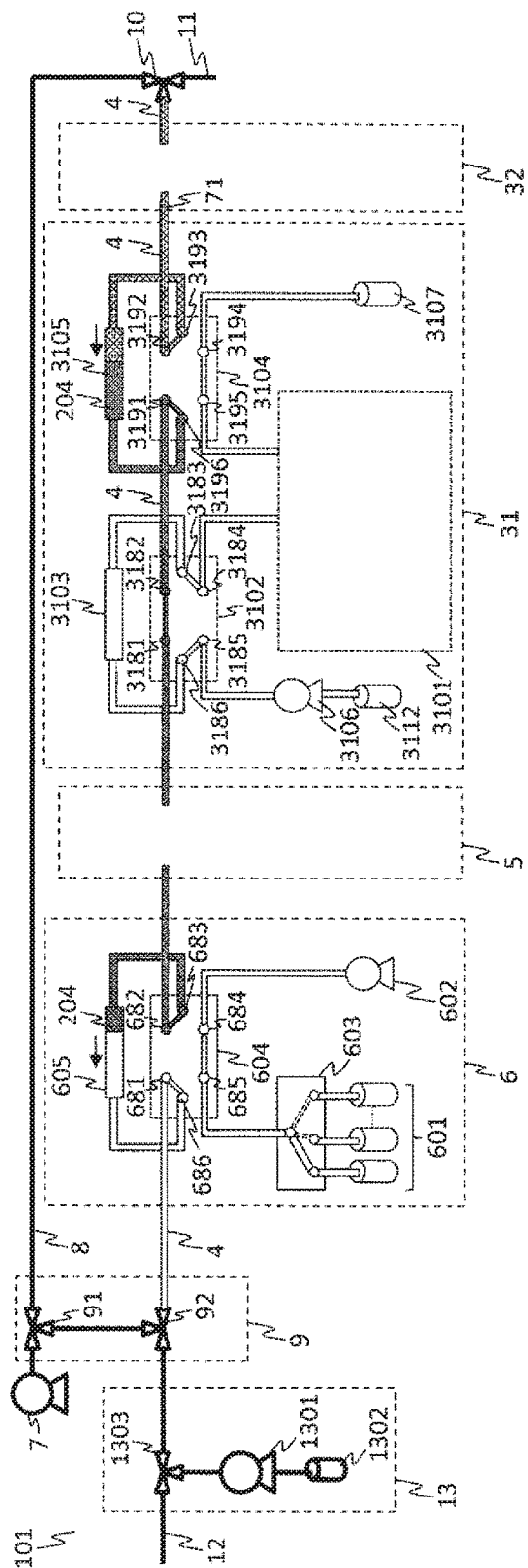
FIG. 12A is a view illustrating a state of conveyance of the sample liquid to a sample liquid conditioning module after the pretreatment illustrated in FIG. 1.
Figure 12B:
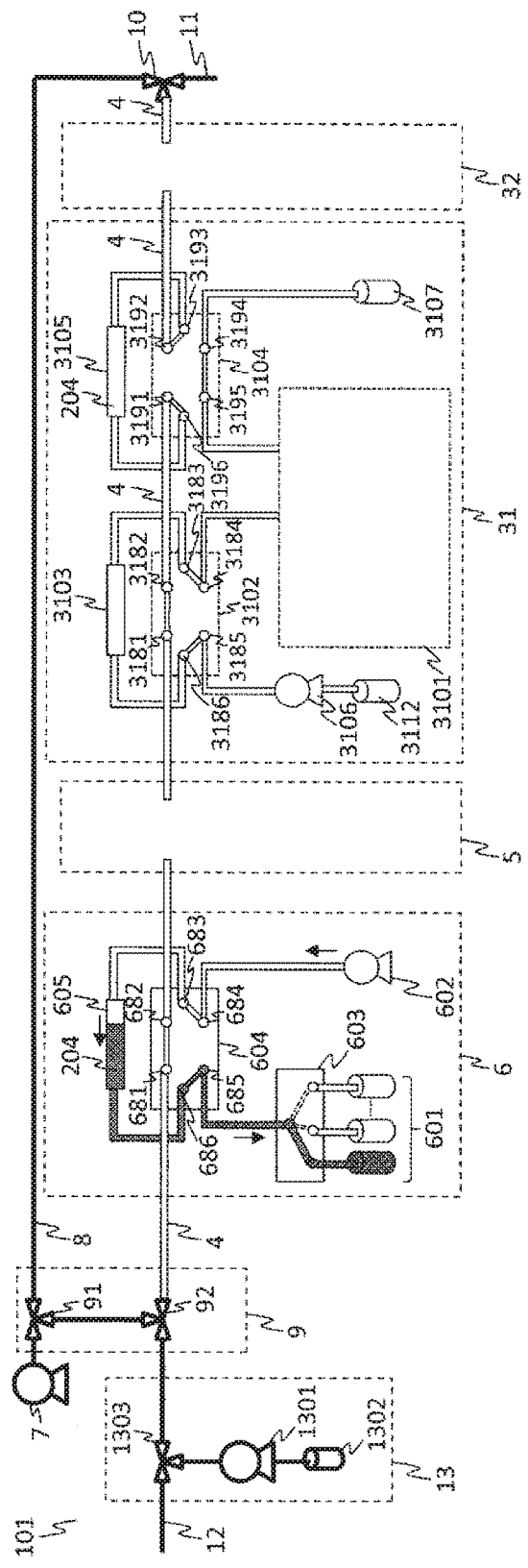
FIG. 12B is a view illustrating a state of an operation of the sample liquid conditioning module after the pretreatment illustrated in FIG. 1.

FIGS. 12(*a*) and 12(*b*) illustrate operational states of the pretreated sample liquid conditioning module 6 illustrated in FIG. 1. FIGS. 12(*a*) and 12(*b*) correspond to Step S117 in FIG. 2.

As illustrated in FIG. 12(*a*), the switching unit 3104 for discharging the sample liquid in the first sample liquid treatment module 31 is switched to the state of communication of the pattern B from the pattern A. In other words, the connection port 3191 and the connection port 3196, the connection port 3192 and the connection port 3193, and the connection port 3194 and the connection port 3195 communicate with each other, respectively, in the switching unit 3104 for discharging the sample liquid.

In addition, the switching unit 604 for conditioning the sample liquid in the pretreated sample liquid conditioning module 6 is switched to the state of communication of the pattern B from the pattern A. In other words, a connection port 681 and a connection port 686, a connection port 682 and a connection port 683, and a connection port 684 and a connection port 685 communicate with each other, respectively, in the switching unit 604 for introducing the sample liquid.

In addition, the three-way valve 91, the three-way valve 92, and the three-way valve 10 are switched such that communication is performed in the following order, the compressor 7, the three-way valve 91, the three-way valve 10, the connection port 3192, the connection port 3193, the sample liquid discharging buffer 3105, the connection port 3196, the connection port 3191, the connection port 682, the connection port 683, the sample liquid conditioning buffer 605, the connection port 686, the connection port 681, the three-way valve 92, the cleaning part 13, and the open end 12. In this state, the compressed air 71 is supplied from the compressor 7 and, thereby, the third-mixed sample liquid 204 in the sample liquid discharging buffer 3105 is conveyed into the sample liquid conditioning buffer 605 through the compressed air flow path 8 as the second flow path. At this time, the third-mixed sample liquid 204 flows into the sample liquid conditioning buffer 605 and, thereby, air present in the sample liquid conditioning buffer 605 until then is discharged through the open end 12.

A method of determining the completion of the filling of the sample liquid conditioning buffer 605 with the third reagent-mixed sample liquid 204 is the same as the method of determining the completion of the filling of the sample liquid introducing buffer 505 with the sample liquid 2 described in FIGS. 5(*a*) to 5(*c*).

Next, as illustrated in FIG. 12(*b*), the switching unit 604 for conditioning the sample liquid is switched to the state of communication of the pattern A from the pattern B. In other words, the connection port 681 and the connection port 682, the connection port 663 and the connection port 684, and the connection port 685 and the connection port 686 communicate with each other, respectively, in the switching unit 604 for introducing the sample liquid. In addition, the selection valve 603 for conditioning the sample liquid is changed such that it is possible to introduce the third reagent-mixed sample liquid 204 in the sample liquid conditioning buffer 605 into a predetermined pretreated sample liquid vessel 601. In this state, the sample liquid conditioning pump 602 performs ejection, the pretreated sample liquid vessel 601 is filled with the third reagent-mixed sample liquid 204. As above, the pretreated sample liquid conditioning module 6 operates and, thereby, the treatment in Step S117 in FIG. 2 is carried out.

(6) Operation of Cleaning Part 13

The cleaning part 13 includes the cleaning liquid sending pump 1301 for sending the cleaning liquid, the cleaning liquid conditioning vessel 1302 for conditioning the cleaning liquid, and the three-way valve 1303. The three-way valve 1303 allows the cleaning liquid to communicate with the three-way valve 92 in the compressed air direction switching part 9 or allows the three-way valve 92 to communicate with the open end 12.

As described above, for example, when the process proceeds to Step S102 from Step S101 illustrated in FIG. 2, the operational state illustrated in FIG. 4(*b*) is switched to the operational state illustrated in FIG. 7. In the state illustrated in FIG. 7, as described above, the switching unit 3102 for introducing the sample liquid and the switching unit 3104 for discharging the sample liquid in the first sample liquid treatment module 31 are both switched to the state of communication of the pattern A. At this time, the connection port 3181 and the connection port 3182 in the switching unit 3102 for introducing the sample liquid and the connection port 3191 and the connection port 3192 in the switching unit 3104 for discharging the sample liquid communicate with each other, respectively, and communicate with the sample liquid conveyance flow path 4. In comparison, a flow path communicating with the sample liquid introducing buffer 3103, the sample liquid treating unit 3101, and the sample liquid discharging buffer 3105 is in a state of being separated from the sample liquid conveyance flow path 4.

Accordingly, in this state, the cleaning liquid sending pump 1301 is driven and the cleaning liquid is sent into the sample liquid conveyance flow path 4 through the three-way valve 1303 and the three-way valve 92, thereby, making it possible to perform cleaning of the sample liquid conveyance flow path 4 at the same time as the treatment by the first sample liquid treatment module 31 (Steps S103 and S104 in FIG. 2).

In this manner, according to the present example, the cleaning liquid sending pump 1301 is driven at the same time as the treatment processes illustrated in FIG. 2, the cleaning liquid flows into the sample conveyance flow path 4 through the three-way valve 1303, and it is possible to clean the sample conveyance flow path 4. In this manner, it is possible to reduce a carry-over between the samples and to improve analysis accuracy.

Further, instead of carrying out the cleaning process at the same time as the treatment processes, an operation is performed so as to combine the cleaning process between the treatment processes. In this case, treatment time is increased; however, the carry-over between the samples is reduced and, thus, it is possible to improve the analysis accuracy.

In the pretreatment device 101 of the present example, it is possible to introduce the sample liquid from the sample conveyance flow path 4 through the switching unit for introducing the sample liquid (for example, the switching unit 3102 for introducing the sample liquid in the first sample liquid treatment module 31) to the sample liquid treating unit (for example, the sample liquid treating unit 3101 in the first sample liquid treatment module 31). In addition, it is possible to discharge the sample liquid treated in the sample liquid treating unit (for example, the sample liquid treating unit 3101) to the sample conveyance flow path 4 through the switching unit for discharging the sample liquid (for example, the switching unit 3104 for the sample liquid in the first sample liquid treatment module 31). In addition, it is possible to dispose a plurality of sample treatment modules in the pretreatment device 101 and, thus, it is possible to arbitrarily perform feature expansion. In addition, it is possible to switch a direction of conveyance of the sample liquid into the sample conveyance flow path 4 by the compressed air direction switching part 9, the three-way valve 10, and the open ends 11 and 12.

Hence, according to the pretreatment device 101 of the present example, it is possible to introduce the sample liquid or the treated sample liquid to an arbitrary sample treatment module connected to the sample liquid conveyance flow path 4 in an arbitrary order.

In this manner, it is possible to realize various types of pretreatment by one pretreatment device. There is no need to perform connection of the sample liquid treatment modules for each pretreatment and, thus, a user can save time and effort.

In addition, since the sample liquid conveyance flow path 4 and the sample liquid treating unit (for example, the sample liquid treating unit 3101) in the sample liquid treatment module (for example, the first sample liquid treatment module 31) is separated and is interrupted by the switching unit for introducing the sample liquid (for example, the switching unit 3102 for introducing the sample liquid) and the switching unit for discharging the sample liquid (for example, the switching unit 3104 for discharging the sample liquid), the compressor or the conveyance flow path, which supplies the compressed air so as to convey the sample liquid in the sample liquid conveyance flow path 4, does not need to have high pressure resistance.

In the present example, the configuration in which the compressed air for conveying the sample liquid is supplied by the compressor 7 is employed; however, the example is not limited thereto, and, for example, a configuration in which system water is supplied by a pump may be employed. In this case, the second flow path 8 is a flow path through which the system water flows.

Example 2

FIG. 13 is a view illustrating an overall configuration of the pretreatment device according to Example 2 of the present invention. The same reference number is assigned to the same component in Example 1 illustrated in FIG. 1. In Example 1, the sending of the sample liquid into the sample liquid treating units 3101 and 3201 in the first sample liquid treatment module 31 and the second sample liquid treatment module 32 is performed by supplying the system water; however, the present example employs a configuration in which the sending is performed by supplying compressed air from the compressor 7, as a difference from Example 1.

As illustrated in FIG. 13, in the first sample liquid treatment module 31 constituting the pretreatment device 102, a two-way valve 3121 is disposed between the compressed air flow path 8 as the second flow path and the switching unit 3102 for introducing the sample liquid. Similarly, in the second sample liquid treatment module 32, a two-way valve 3221 is disposed between the compressed air flow path 8 and the switching unit 3202 for introducing the sample liquid.

In the case where the sample liquid is sent in the first sample liquid treatment module 31, for example, a case where the same operation as the operation of the first sample liquid treatment module 31 is performed in the derivatization treatment of the amino acid sample described in FIG. 7 in Example 1 is described as an example. In FIG. 13, the three-way valve 91 is switched such that communication is performed with the compressor 7, the three-way valve 91, the two-way valve 3121, and the switching unit 3102 for introducing the sample liquid. In addition, the two-way valve 3121 is switched to an opened state and, thereby, the sample liquid 2 in the sample liquid introducing buffer 3103 of the first sample liquid treatment module 31 is sent into the sample liquid treating unit 3101 by the compressed air 71 which is supplied from the compressor 7.

The second sample treatment module 32 operates in the same way as the first sample liquid treatment module 31. In the configuration, it is possible to simplify a configuration of a device, compared to Example 1 in which the sample liquid sending pump 3106 and the sample liquid sending pump 3206 need to be provided. In addition, it is possible to achieve the same effects as of Example 1 also in the present example.

As a sending mechanism of the sample liquid in the sample liquid treatment module, whether the sample liquid sending pump illustrated in Example 1 is used or the compressed air illustrated in the present example is used, may vary for each of the sample liquid treatment module, or may be selected based on sending accuracy required in the sample liquid treating unit in the sample liquid treatment module.

Example 3

FIG. 14 is a view illustrating an overall configuration of an analysis system including the pretreatment device 103 and the analysis device 14 according to Example 3 of the present invention. In FIG. 14, the same reference number is assigned to the same component as in the pretreatment device 101 illustrated in FIG. 1. The present example differs from Example 1 in that, instead of the sample liquid conditioning module 6 for conditioning the pretreated sample liquid, a configuration in which the sample liquid transport module 13 is disposed and the pretreated sample liquid is conveyed to the analysis device 14 by the sample liquid transport module 13.

In FIG. 14, the sample liquid introduction module 5, the first sample liquid treatment module 31, the second sample liquid treatment module 32, the compressed air direction switching part 9, and the cleaning part 13 are the same as in Example 1, and description thereof is omitted. A sample liquid transporting buffer 1305 is filled with the third reagent-mid sample liquid 204 by the first sample liquid treatment module 31 and the state of communication is switched in the same way as in Example 1 by a switching unit 1304 for transporting the sample liquid. A method of determining the completion of the filling of the sample liquid transporting buffer 1305 with the third reagent-mixed sample liquid 204 is the same as the method of determining the completion of the filling of the sample liquid introducing buffer 505 with the sample liquid described in FIGS. 5(*a*) to 5(*c*) in Example 1.

After the sample liquid transporting buffer 105 is completely filled with the third reagent-mixed sample liquid 204, the state of communication is switched by the switching unit 1304 for transporting the sample liquid and the sample liquid transporting pump 1302 performs ejection, thereby sending the third reagent-mixed sample liquid 204 into the analysis device 14. In other words, in the configuration of the present example, the sample liquid pretreated by the pretreatment device 103 is directly conveyed to the analysis device 14 by the sample liquid transport module 13.

According to the present example, it is possible to analyze the sample in the analysis device 14 immediately after the pretreatment by the pretreatment device 103 is completed. In this manner, in a case of analyzing a sample in which decomposition progresses after the pretreatment, it is possible to improve analysis accuracy, compared to the configuration of Example 1. In the present example, it is possible to achieve the same effects as in Example 1.

Further, the present invention is not limited to the examples described above, and various modification examples are included. For example, the example described above is described in detail in order to clearly describe the present invention and the present invention is not limited to an example having all of the configurations described. It is possible to replace a part of the configuration of one example with a configuration of another example. In addition, it is possible to add a configuration of an example to the configuration of another example. In addition, it is possible to perform addition, removal, and replacement of a part of the configuration of the examples with a configuration of another example.

REFERENCE SIGNS LIST

2 . . . sample liquid
4 . . . sample liquid conveyance flow path
5 . . . sample liquid introduction module
6 . . . sample liquid conditioning module
7 . . . compressor
8 . . . compressed air flow path
9 . . . compressed air direction switching part
10 . . . three-way valve
11, 12 . . . open end
13 . . . cleaning part
14 . . . analysis device
31 . . . first sample liquid treatment module
32 . . . second sample liquid treatment module
101, 102, 103 . . . pretreatment device
3101, 3201 . . . sample liquid treating unit
3102, 3202 . . . switching unit for introducing sample liquid
3104, 3204 . . . switching unit for discharging sample liquid
3103, 3203 . . . sample liquid introducing buffer
3105, 3205 . . . sample liquid discharging buffer

The invention claimed is:

1. A pretreatment device for a sample for analysis comprising, at least:
a plurality of sample liquid modules for introducing a sample liquid or for carrying out prescribed pretreatment on the sample liquid, the plurality including at least three modules;
a two-directional first flow path for conveying the sample liquid or the pretreated sample liquid between the plurality of sample liquid modules;
a second flow path for injecting compressed air into the two-directional first flow path;
a three-way valve at one end of the two-directional first flow path;
a cleaning part for cleaning the three-way valve, wherein the cleaning part passes a cleaning agent through the two-directional first flow path during transfer of the sample liquid into the plurality of sample liquid modules; and
a compressed air direction switching part for switching the conveyance direction of the sample liquid or the pretreated sample liquid in the two-directional first flow path; and
a compressor to power the compressed air direction switching part for switching the conveyance direction of the sample liquid or the pretreated sample liquid,
wherein the plurality of sample liquid modules have an introduction flow path for introducing the sample liquid or the pretreated sample liquid from the two-directional first flow path, a discharge flow path for sending the sample liquid or the pretreated sample liquid to the two-directional first flow path, and a flow path switching part for switching the state of communication with the two-directional first flow path of the introduction flow path and the discharge flow path,
each of the plurality of sample liquid modules being separated from adjacent ones of the plurality of sample liquid modules by respective portions of the two-directional first flow path, and
the two-directional first flow path is configured to permit bi-directional transfer of the sample liquid from one of the plurality of sample liquid modules to any other of the plurality of sample liquid modules.

2. The pretreatment device for a sample for analysis according to claim 1,
wherein the plurality of sample liquid modules include a sample liquid introducing buffer for accumulating the sample liquid which is introduced through the two-directional first flow path, a sample liquid treating unit for carrying out prescribed pretreatment on the sample liquid, and a sample liquid discharging buffer for accumulating the sample liquid from the sample liquid treating unit, and
wherein the flow path switching part includes
a first switching unit for introducing the sample liquid that switches between a flow path for introducing the sample liquid to the sample liquid introducing buffer through the two-directional first flow path and a flow path for introducing the sample liquid to the sample liquid treating unit from the sample liquid introducing buffer, and
a second switching unit for discharging the sample liquid that switches between a flow path for introducing the sample liquid to the sample liquid discharging buffer from the sample liquid treating unit, and a flow path for sending the sample liquid to the first flow path from the sample liquid discharging buffer.

3. The pretreatment device for a sample for analysis according to claim 2, further comprising:
a detection unit that detects filling, with the sample liquid, the sample liquid introducing buffer and the sample liquid discharging buffer,
wherein the first switching unit for introducing the sample liquid and the second switching unit for discharging the sample liquid operate based on a filling detection result.

4. The pretreatment device for a sample for analysis according to claim 3,
wherein the detection unit detects the filling with the sample liquid by using an output from a light sensor disposed on a flow path on the discharge side of the sample liquid introducing buffer and the sample liquid discharging buffer or by using a potential difference between electrodes.

5. The pretreatment device for a sample for analysis according to claim 3,
    wherein the sample liquid introducing buffer and the sample liquid discharging buffer include a region, in which the flow path has a widened width, between a sample liquid introducing flow path and a sample liquid discharging flow path,
    wherein a first orifice that decreases the width of the flow path is formed at a connection section between the sample liquid introducing flow path and the region or in the vicinity of the connection section, and a second orifice that decreases the width of the flow path is formed at a connection section between the sample liquid discharging flow path and the region or in the vicinity of the connection section, and
    wherein the detection unit is a pressure sensor that detects a pressure loss through the first and second orifices.

6. The pretreatment device for a sample for analysis according to claim 2,
    wherein the cleaning part is connected to one side of a communication section between the two-directional first flow path and the second flow path through a switching valve, and
    wherein the cleaning part includes a cleaning liquid conditioning vessel for containing a cleaning liquid and a cleaning liquid sending pump, and the cleaning liquid is sent to the two-directional first flow path through the switching valve.

7. The pretreatment device for a sample for analysis according to claim 6,
    wherein, in a state in which the switching unit for introducing the sample liquid performs switching to a flow path for introducing the sample liquid to the sample liquid treating unit from the sample liquid introducing buffer, and in a state in which the switching unit for discharging the sample liquid performs switching to a flow path for introducing the sample liquid to the sample liquid discharging buffer from the sample liquid treating unit, the cleaning part sends a cleaning liquid to the two-directional first flow path through the switching valve.

8. The pretreatment device for a sample for analysis according to claim 2,
    wherein the plurality of sample liquid modules include a sample liquid sending pump for supplying system water to the sample liquid introducing buffer, and
    wherein, in a state in which the switching unit for introducing the sample liquid performs switching to a flow path for introducing the sample liquid to the sample liquid treating unit from the sample liquid introducing buffer, the system water is supplied to the sample liquid introducing buffer by the sample liquid sending pump and the sample liquid accumulated in the sample liquid introducing buffer is introduced to the sample liquid treating unit.

9. The pretreatment device for a sample for analysis according to claim 2, further comprising:
    a two-way valve that is disposed between the second flow path and the switching unit for introducing the sample liquid,
    wherein, in a state in which the switching unit for introducing the sample liquid performs switching to a flow path for introducing the sample liquid to the sample liquid treating unit from the sample liquid introducing buffer, the compressed air or the system water is supplied to the sample liquid introducing buffer through the second flow path through the two-way valve, and the sample liquid accumulated in the sample liquid introducing buffer is introduced to the sample liquid treating unit.

10. An analysis system comprising:
    a pretreatment device including, at least
        a plurality of sample liquid modules for introducing a sample liquid or carrying out prescribed pretreatment on the sample liquid, the plurality including at least three modules,
        a two-directional first flow path for conveying the sample liquid or the pretreated sample liquid between the plurality of sample liquid modules,
        a second flow path for injecting compressed air into the two-directional first flow path;
        a three-way valve at one end of the two-directional first flow path;
        a cleaning part for cleaning the three-way valve, wherein the cleaning part passes a cleaning agent through the two-directional first flow path during transfer of the sample liquid into the plurality of sample liquid modules; and
        a compressed air direction switching part for switching the conveyance direction of the sample liquid or the pretreated sample liquid in the two-directional first flow path; and
        a compressor to power the compressed air direction switching part for switching the conveyance direction of the sample liquid or the pretreated sample liquid,
        the plurality of sample liquid modules having an introduction flow path for introducing the sample liquid or the pretreated sample liquid from the first flow path, a discharge flow path for sending the sample liquid or the pretreated sample liquid to the two-directional first flow path, and a flow path switching part for switching the state of communication with the two-directional first flow path of the introduction flow path and the discharge flow path, each of the plurality of sample liquid modules being separated from adjacent ones of the plurality of sample liquid modules by respective portions of the two-directional first flow path, and
    the two-directional first flow path is configured to permit bi-directional transfer of the sample liquid from one of the plurality of sample liquid modules to any other of the plurality of sample liquid modules; and
    an analysis device that introduces the pretreated sample liquid from the pretreatment device and performs prescribed analysis.

11. The analysis system according to claim 10,
    wherein the pretreatment device includes a sample liquid transport module, and
    wherein the sample liquid transport module includes
        a sample liquid transporting buffer for accumulating the pretreated sample liquid which is introduced through the two-directional first flow path, and
        a switching unit for sample liquid transport that switches between a flow path for introducing the pretreated sample liquid to the sample liquid transporting buffer through the two-directional first flow path and a flow path for sending the pretreated sample liquid to the analysis device from the sample liquid transporting buffer.

12. The analysis device according to claim 11,
wherein the plurality of sample liquid modules include a sample liquid introducing buffer for accumulating the sample liquid which is introduced through the two-directional first flow path, a sample liquid treating unit for carrying out prescribed pretreatment on the sample liquid, and a sample liquid discharging buffer for accumulating the sample liquid from the sample liquid treating unit, and
wherein the flow path switching part includes
a first switching unit for introducing the sample liquid that switches between a flow path for introducing the sample liquid to the sample liquid introducing buffer through the two-directional first flow path and a flow path for introducing the sample liquid to the sample liquid treating unit from the sample liquid introducing buffer, and
a second switching unit for discharging the sample liquid that switches between a flow path for introducing the sample liquid to the sample liquid discharging buffer from the sample liquid treating unit, and a flow path for sending the sample liquid to the two-directional first flow path from the sample liquid discharging buffer.

* * * * *